United States Patent
Irla et al.

(10) Patent No.: US 11,351,226 B2
(45) Date of Patent: Jun. 7, 2022

(54) METHODS OF BOOSTING THYMIC REGENERATION IN PATIENTS SUFFERING FROM A THYMIC INJURY BY USING RANKL

(71) Applicants: INSERM (INSTITUT NATIONAL DE LA SANTÉ ET DE LA RECHERCHE MÉDICALE), Paris (FR); UNIVERSITÉ D'AIX MARSEILLE, Marseilles (FR); CENTRE NATIONAL DE LA RECHERCHE SCIENTIFIQUE (CNRS), Paris (FR)

(72) Inventors: Magali Irla, Marseilles (FR); Noella Lopes, Marseilles (FR)

(73) Assignees: INSERM (INSTITUT NATIONAL DE LA SANTE ET DE LA RECHERCHE MEDICALE), Paris (FR); UNIVERSITE D'AIX MARSEILLE, Marseilles (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 16/488,849

(22) PCT Filed: Feb. 26, 2018

(86) PCT No.: PCT/EP2018/054704
§ 371 (c)(1),
(2) Date: Aug. 26, 2019

(87) PCT Pub. No.: WO2018/154122
PCT Pub. Date: Aug. 30, 2018

(65) Prior Publication Data
US 2020/0009224 A1 Jan. 9, 2020

(30) Foreign Application Priority Data
Feb. 27, 2017 (EP) .................................. 17305214

(51) Int. Cl.
*A61K 38/17* (2006.01)
*A61P 37/00* (2006.01)
*A61K 31/663* (2006.01)

(52) U.S. Cl.
CPC ........ *A61K 38/1793* (2013.01); *A61K 31/663* (2013.01); *A61P 37/00* (2018.01); *C07K 2319/30* (2013.01)

(58) Field of Classification Search
None
See application file for complete search history.

(56) References Cited

U.S. PATENT DOCUMENTS

2014/0248235 A1   9/2014   Dudakov et al.

FOREIGN PATENT DOCUMENTS

| KR | 20090118704 | * 11/2009 | ............. A61K 38/00 |
| WO | WO/2016/069911 | * 5/2016 | ............... C12N 5/10 |

OTHER PUBLICATIONS

Hauri-Hohl et al., Donor T-cell alloreactivity against host thymic epithelium limits T-cell development after bone marrow transplantation. Blood, 109, 4080-4088, 2007. (Year: 2007).*
Izumi Ohigashi et al: "Effects of RANKL on the thymic medulla: Highlights", European Journal of Immunology, vol. 41, No. 7, Jun. 27, 2011, pp. 1822-1827.
Hee-Woo Lee et al: "RANKL stimulates proliferation, adhesion and IL-7 expression of thymic epithelial cells", Experimental and Molecular Medicine, vol. 40, No. 1, Jan. 1, 2008, pp. 59-70.
Hollander G A et al: "Emerging strategies to boost thymic function", Current Opinion in Pharmacology, Elsevier Science Publishers, NL, vol. 10, No. 4, Aug. 1, 2010, pp. 443-453.

* cited by examiner

*Primary Examiner* — Elly-Gerald Stoica
(74) *Attorney, Agent, or Firm* — WC&F

(57) ABSTRACT

Cytoablative treatments lead to severe damages on thymic epithelial cells (TECs), which result in delayed de novo thymopoïesis and a prolonged period of T-cell immunodeficiency. Understanding the mechanisms that govern thymic regeneration is of paramount interest for the recovery of a functional immune system notably after bone marrow transplantation (BMT). Here, the inventors show that administration of RANK ligand (RANKL) after total body irradiation and BMT boosts thymic regeneration. Notably, this treatment is also beneficial upon BMT in aged individuals. The inventors show that RANKL can improve thymopoiesis in aged individuals affected by thymic involution. Finally, the inventors show that RANK receptor is conserved in the human thymus. Accordingly, one aspect of the present invention relates to a method of boosting thymic regeneration in a patient suffering from a thymic injury comprising administering to the subject a therapeutically effective amount of a RANKL polypeptide.

Figure 1:
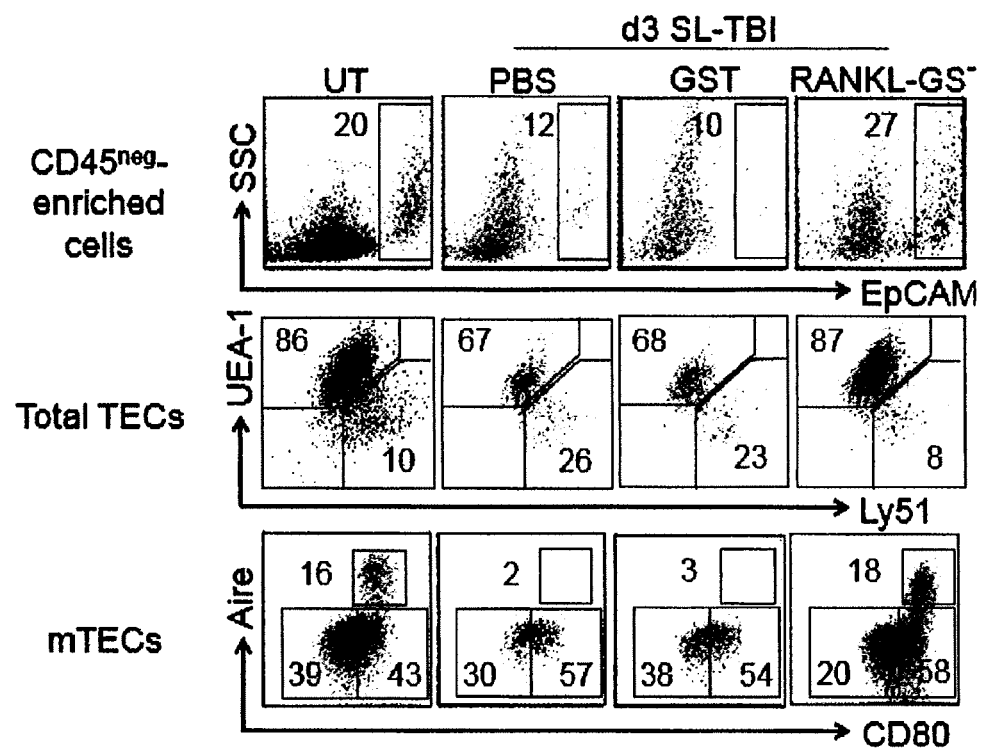
Figure 1:
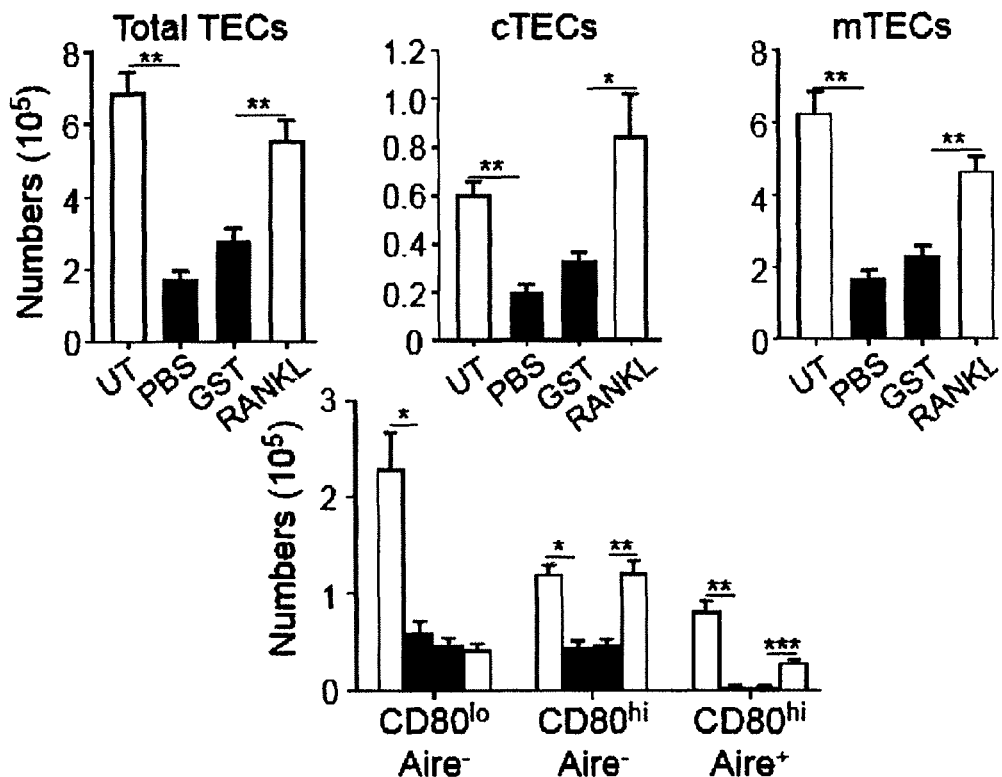

21 Claims, 15 Drawing Sheets
Specification includes a Sequence Listing.

METHODS OF BOOSTING THYMIC REGENERATION IN PATIENTS SUFFERING FROM A THYMIC INJURY BY USING RANKL

FIELD OF THE INVENTION

The present invention relates to a method of boosting thymic regeneration in patients suffering from a thymic injury based on the administration of RANKL.

BACKGROUND OF THE INVENTION

The thymus controls the generation of T lymphocytes. Cortical thymic epithelial cells (cTECs) support the differentiation of T-cell progenitors and the conversion of CD4+CD8+ double-positive (DP) thymocytes into CD4+CD8− and CD4−CD8+ single-positive (SP) cells (1). Medullary TECs (mTECs) purge the TCR repertoire of hazardous autoreactive T cells by expressing thousands of tissue-restricted antigens (TRAs), which are controlled by Aire (Autoimmune Regulator) and Fezf2 (Forebrain Expressed Zinc Finger 2) factors (2-5). Reciprocally, thymocytes sustain TEC differentiation and organization. This complex interplay is referred to as thymic crosstalk (6, 7).

Cytoablative treatments such as radiation or chemotherapy, used to prepare patients notably to bone marrow (BM) transplantation (BMT), severely affect not only hematopoietic cells but also TECs, which results in delayed T-cell reconstitution (8-11). Thymic injury triggered by total body irradiation (TBI) leads to profound alterations characterized by a drastic reduction in the cortex resulting from the massive depletion of DP thymocytes and a significant decrease in the medulla (12). Alterations in TEC ultrastructure and a reduction in some stromal cells have also been reported (10, 13).

The recovery of a fully competent T-cell compartment is therefore a prolonged process that is considerably delayed compared to that of myeloid, NK or B cells (14). This period of compromised immunity is prompt to serious clinical consequences such as opportunistic infections, autoimmunity or tumor relapse and could lead to post-transplant morbidity and mortality (8, 15-18). Identifying an effective treatment that acts at several levels by improving (1) the regeneration of TECs, which are critical for the renewal of stromal niches, (2) the recovery of cortical and medullary TECs, which control the different steps of thymopoiesis and (3) thymus homing of T-cell progenitors, which is important for T-cell recovery, is of paramount clinical interest to optimally boost thymic regeneration (19-21).

RANKL, a TNF family member, has emerged as an important regulator of epithelial cell growth and differentiation in different tissues such as mammary glands during pregnancy (22), the renewal and epidermal growth of the hair follicles (23) or M-cell differentiation from intestinal epithelial cells in Payer's patches (24). In the embryonic thymus, RANKL provided by lymphoid tissue inducer (LTi) cells and invariant Vγ5+TCR+ T-cell progenitors promotes the emergence of Aire+ mTECs, which mediate T-cell tolerance (4, 25, 26). In the postnatal thymus, RANKL produced by SP thymocytes enhances numbers of Aire+ mTECs and the size of the medulla (6, 27-31). However, although RANKL is a potent inducer of mTEC differentiation at steady state, whether and how RANKL drives thymic regeneration upon BMT remain unknown.

SUMMARY OF THE INVENTION

The present invention relates to methods of boosting thymic regeneration in patients suffering from a thymic injury. In particular, the present invention is defined by the claims.

DETAILED DESCRIPTION OF THE INVENTION

Cyto ablative treatments lead to severe damages on thymic epithelial cells (TECs), which result in delayed de novo thymopoïesis and a prolonged period of T-cell immunodeficiency. Understanding the mechanisms that govern thymic regeneration is of paramount interest for the recovery of a functional immune system notably after bone marrow transplantation (BMT). Here, the inventors show that RANK ligand (RANKL) is strongly upregulated in LTi cells and to a lesser extent in CD4+ SP cells during the early phase of thymic regeneration. Importantly, whereas the administration of a neutralizing RANKL antibody severely alters TEC regeneration, the administration of RANKL protein after total body irradiation and BMT boosts the regeneration of cortical and medullary TEC subsets and thymic epithelial progenitor-enriched cells (TEPCs). RANKL treatment also enhances the thymus homing of lymphoid progenitors and de novo thymopoiesis. The inventors further found that RANKL administration increases specifically in LTi cells, lymphotoxin α (LTα), which is critical for both TEC regeneration and T-cell reconstitution after BMT. Notably, this treatment is also beneficial upon BMT in aged individuals. This study indicates that RANKL would be clinically useful to improve T-cell function recovery after BMT not only in young but also in aged individuals by controlling multiple facets of thymic regeneration.

Accordingly the first object of the present invention relates to a method of boosting thymic regeneration in a patient suffering from a thymic injury comprising administering to the subject a therapeutically effective amount of a RANKL polypeptide.

As used herein, the term "thymic injury" has its general meaning in the art and refers to any insult of the thymic epithelial cells (TEC) and T cells. Typical insult includes cytoablative therapy (e.g. required to prepare patients to bone marrow transplantation (BMT)), complications related to HIV/AIDS, aging process, malnutrition, and radiation poisoning due to nuclear disaster. The term also includes age-related thymic involution, i.e. the progressive shrinking of the thymus with age.

The thymic injury may result from irradiation, for instance as medical treatment. Any subject/patient who receives irradiation may be treated with the method of the invention (i.e by administrating RANKL). Examples of diseases which are in part treated with irradiation included but are not limited to: cancers such as multiple myeloma, non-Hodgkin's lymphoma, Hodglin's disease, acute myeloid leukemia, neuroblastoma, ovarian cancer, germ-cell tumors, acute lymphoblastic leukemia, chronic myeloid leukemia, myelodysplasic syndromes, myeloproliferative disorders, chronic lymphocytic leukemia, juvenile chronic myeloid leukemia, and others diseases such as autoimmune disorders, amyloidosis, aplastic anemia, paroxysmal nocturnal hemoglobinuria, Fanconi's anemia, Blackfan-Diamond anemia, thalassemia major, sickle cell anemia, severe combined immunodeficiency, Wiskott-Aldrich syndrome, inborn errors of metabolism.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

Typically, the term "patient" or "subject" is selected from the group consisting of children, young adults, middle aged adults, and the elderly adults. In some embodiments, the patient is an elderly patient, i.e. an adult patient sixty-five years of age or older. In particular, the administration of RANKL in elderly individuals is particular suitable for reversing the effects of aging on thymic involution. Indeed, the aging process results on an immune system which is less effective/functional which gives rise to cancers, infections, autoimmune diseases, etc. Typically, the patient (or "subject") is a human.

In some embodiments, the patient suffers from cancer. As used herein, the term "cancer" has its general meaning in the art and includes, but is not limited to, solid tumors and blood borne tumors. The term cancer includes diseases of the skin, tissues, organs, bone, cartilage, blood and vessels. The term "cancer" further encompasses both primary and metastatic cancers. Examples of cancers that may treated by methods and compositions of the invention include, but are not limited to, cancer cells from the bladder, blood, bone, bone marrow, brain, breast, colon, esophagus, gastrointestinal, gut, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extramammary paraganglioma, malignant; pheochromocytoma; glomangio sarcoma; malignant melanoma; amelanotic melanoma; superficial spreading melanoma; malign melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangio sarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the patient has undergone a cytoablative therapy which caused thymic injury. The term "cytoablative therapy" has its general meaning in the art and refers to therapy that induce cytoablative effects on rapidly-proliferating cells via several different mechanisms, ultimately leading to cell cycle arrest and/or cellular apoptosis. Typically cytoablative therapy includes chemotherapy and radiotherapy.

As used herein, the term "radiotherapy" has its general meaning in the art and refers to the medical use of ionizing radiation, generally as part of cancer treatment to control or kill malignant cells.

As used herein the term "chemotherapy" has its general meaning in the art and refers to the medical use of chemotherapeutic agents effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a carnptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estrarnustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33: 183-186 (1994); dynemicin, including dynemicin A; an esperamicin; as well as neocarzino statin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; amino levulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylarnine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.].) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are antihormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and phannaceutically acceptable salts, acids or derivatives of any of the above.

In some embodiments, the administration of the RANKL polypeptide is performed after bone marrow transplantation. As used herein, the term "bone marrow transplantation" or "stem cell transplantation" used herein should be considered as interchangeable, referring to the transplantation of stem cells in some form to a recipient. The stem cells do not necessarily have to be derived from bone marrow, but could also be derived from other sources such as umbilical cord blood. As used herein, the terms "hematopoietic stem cell transplantation" or "HSCT" refer to a component of the treatment of a wide array of hematologic disorders. Generally, there are two types of HSCTs: autologous and allogeneic transplantation. As used herein, the term "allogeneic" refers to deriving from, originating in, or being members of the same species, where the members are genetically related or genetically unrelated but genetically similar. An "allogeneic transplant" refers to transfer of cells or organs from a donor to a recipient, where the recipient is the same species as the donor. Allogeneic transplantation involves infusion of donor stem cells, typically using a donor that matches the recipient's MHC. As used herein, the term "autologous" refers to deriving from or originating in the same subject or patient. An "autologous transplant" refers to collection and retransplant of a subject's own cells or organs.

The method of the present invention is particularly suitable for preventing immunodeficiency linked to cytoablative conditioning. The method of the present invention is particularly suitable for the prophylactic treatment of infectious diseases, autoimmunity or cancer relapse in particular by boosting/enhancing the recovery of T-cell functions in a long-term manner.

The present invention also relates to a method for the prophylactic treatment of infectious diseases, autoimmunity or cancer relapse in particular by boosting/enhancing the recovery of T-cell functions in a long-term manner in a subject in need thereof comprising administering to the subject a therapeutically effective amount of a RANKL polypeptide.

As used herein, the term "prophylactic treatment" refers to any medical or public health procedure whose purpose is to prevent a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a subject with the disease. It is also to be appreciated that the various modes of treatment or prevention of medical conditions as described are intended to mean "substantial," which includes total but also less than total treatment or prevention, and wherein some biologically or medically relevant result is achieved.

As used herein the term "infectious disease" includes any infection caused by viruses, bacteria, protozoa, molds or fungi. In some embodiments, the infectious disease is an opportunistic infection. As used herein, the term "opportunistic infection" refers to bacterial, viral, fungal or protozoan infection caused by opportunistic pathogens that may or may not cause diseases in healthy hosts having a functioning immune system. These pathogens may cause an opportunistic infection since a compromised immune system presents an "opportunity" for such pathogens to thrive in an immunocompromised subject. Non-limiting examples of viral infections include Herpes simplex virus (HSV) infections, Cytomegalovirus (CMV) infections, Varicella-zoster virus (VZV) infections, Human herpes virus 6 (HHV6) infections, Epstein-Barr virus (EBV) infections, respiratory virus infections (such as respiratory syncytial virus (RSV), parainfluenza virus, rhinovirus, and influenza virus) and adenovirus infections. Non-limiting examples of bacterial infections include Gram-negative bacteria infections such as *Escherichia* (e.g. *Escherichia coli*), *Salmonella*, *Shigella*, and other Enterobacteriaceae, *Pseudomonas* (e.g. *Pseudomonas aeruginosa*), *Moraxella*, *Helicobacter*, and *Legionella* infections. Non-limiting examples of fungal infections include *Aspergillus* infection (e.g. *Aspergillus fumigatus*), *Candida* infection (e.g. *Candida albicans* and non-*albicans Candida*) and other emerging fungi infections including *Trichosporon*, *Alternaria*, *Fusarium*, and *Mucorales* infections.

As used herein, the term "autoimmunity" is used to describe the process by which the body generates an immune response to self-antigens. Exemplary autoimmune diseases affecting humans include rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (for example, Crohn's disease and ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, acquired hemophilia, thrombotic thrombocytopenic purpura and the like.

As used herein, the term "RANKL" has its general meaning in the art and refers to Receptor Activator of Nuclear factor Kappa-B Ligand (RANKL) which is a protein that in humans is encoded by the TNFSF11 gene (Gene ID: 8600). The term RANKL is also known as tumor necrosis factor ligand superfamily member 11 (TNFSF11), TNF-related activation-induced cytokine (TRANCE), osteoprotegerin ligand (OPGL), and osteoclast differentiation factor (ODF), sOdf; CD254; OPTB2; TNLG6B; and hRANKL2. Exemplary amino acid sequences are represented by SEQ ID NO:1 (NCBI reference sequence NP_003692.1) and SEQ ID NO:2 (NCBI reference sequence NP_143026.1). RANKL is a compound that permits the regeneration of all TEC subtypes, i.e. cortical and medullary TECs as well as their progenitors, which are critical for the renewal of stromal niches. RANKL acts also on thymus homing of early thymic progenitors (ETPs) that give rise to the T-cell lineage. Thus, by acting on the availability size of stromal compartment and on the thymus homing of T-cell progenitors, RANKL importantly boosts de novo thymopoïesis.

```
                                                                SEQ ID NO: 1
  1  mrrasrdytk ylrgseemgg gpgaphegpl happppaphq ppaasrsmfv allglglgqv
 61  vcsvalffyf raqmdpnris edgthciyri lrlhenadfq dttlesqdtk lipdscrrik
121  qafggavqke lghivgsqhi raekamvdgs wldlakrskl eaqpfahlti natdipsgsh
181  kvslsswyhd rgwakisnmt fsngklivnq dgfyylyani cfrhhetsgd lateylqlmv
241  yvtktsikip sshtlmkggs tkywsgnsef hfysinvggf fklrsgeeis ievsnpslld
301  pdqdatyfga fkvrdid SEQ ID NO: 2
  1  mdpnrisedg thciyrilrl henadfqdtt lesqdtklip dscrrikqaf qgavqkelqh
 61  ivgsqhirae kamvdgswld lakrskleaq pfahltinat dipsgshkvs lsswyhdrgw
121  akisnmtfsn gklivnqdgf yylyanicfr hhetsgdlat eylqlmvyvt ktsikipssh
181  tlmkggstky wsgnsefhfy sinvggffkl rsgeeisiev snpslldpdg datyfgafkv
241  rdid
```

As used herein, the term "RANKL polypeptide" refers to a polypeptide comprising an amino acid sequence having at least 80% of identity with SEQ ID NO:1 or SEQ ID NO:2. According to the invention a first amino acid sequence having at least 80% of identity with a second amino acid sequence means that the first sequence has 80; 81; 82; 83; 84; 85; 86; 87; 88; 89; 90; 91; 92; 93; 94; 95; 96; 97; 98; 99 or 100% of identity with the second amino acid sequence. Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

In some embodiments, the RANKL polypeptide of the present invention is fused to an immunoglobulin domain so as to form an immunoadhesin. As used herein, the term "immunoadhesin" designates antibody-like molecules which combine the binding specificity of the RANKL polypeptide with the effector functions of immunoglobulin constant domains. In some embodiments, the immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM. In some embodiments, the immunoglobulin sequence is an immunoglobulin constant domain (Fc region). Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use. The artisan skilled in the art can easily select the most appropriate Fc domain (Chan A C, Carter P J. Therapeutic antibodies for autoimmunity and inflammation. Nat Rev Immunol. 2010 May 10(5):301-16. doi: 10.1038/nri2761. Review.). In some embodiments, the Fc region includes or not a mutation that inhibits complement fixation and/or Fc receptor binding (Zheng et al, Transplantation. 2006 Jan. 15; 81(1):109-16). In some embodiments, the Fc region is a native sequence Fc region. In some embodiments, the Fc region is a variant Fc region. In some embodiments, the Fc region is a functional Fc region. As used herein, the term "Fc region" is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. In some embodiments, the adhesion portion and the immunoglobulin sequence portion of the immunoadhesin are linked by a minimal linker.

According to the invention, the RANKL polypeptide is produced by conventional automated peptide synthesis methods or by recombinant expression. General principles for designing and making proteins are well known to those of skill in the art.

In some embodiments, it is contemplated that the RANKL polypeptide is modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain. For example, Pegylation is a well-established and validated approach for the modification of a range of polypeptides. The benefits include among others: (a) markedly improved circulating half-lives in vivo due to either evasion of renal clearance as a result of the polymer increasing the apparent size of the molecule to above the glomerular filtration limit, and/or through evasion of cellular clearance mechanisms; (b) reduced antigenicity and immunogenicity of the molecule to which PEG is attached; (c) improved pharmacokinetics; (d) enhanced proteolytic resistance of the conjugated protein; and (e) improved thermal and mechanical stability of the PEGylated polypeptide.

By a "therapeutically effective amount" is meant a sufficient amount of RANKL polypeptide to provide therapeutic effects at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular patient will depend upon a variety of factors including the disease being treated and the severity of the disease; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In some embodiments, the RANKL polypeptide is administered to the patient in combination with bisphosphonate to prevent bone resorption. As used herein, the term "bisphosphonate" means compounds characterised by two C—PO3 2-bonds. If the two bonds are located on the same carbon atom, the compounds are called geminal bisphosphonates. It should be noted that the term "bisphosphonate" as used herein are meant to also encompass diphosphonates, biphosphonic acids, and diphosphonic acids, as well as salts and derivatives of these materials.

Typically, the RANKL polypeptide is administered to the patient in the form of a pharmaceutical composition. The pharmaceutical composition comprises the RANKL polypeptide optionally with a pharmaceutically acceptable carrier or excipient. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. In some embodiments, the pharmaceutical composition is administered intrathymically. Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The RANKL polypeptide can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. The RANKL polypeptide may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will be further illustrated by the following figures and examples. However, these examples and figures should not be interpreted in any way as limiting the scope of the present invention.

FIGURES

FIG. 1. In vivo administration of RANKL substantially improves TEC regeneration after TBI. Flow cytometry profiles and numbers of total TECs (EpCAM$^+$), cTECs (UEA-1$^-$Ly51$^+$), mTECs (UEA-1$^+$Ly51$^-$) and mTEC subsets (CD80$^{lo}$Aire$^-$, CD80$^{hi}$Aire$^-$ and CD80$^{hi}$Aire$^+$) in UT WT mice or treated with PBS, GST or RANKL during three days upon SL-TBI.

FIG. 2: RANKL boosts TEC regeneration and de novo thymopoïesis in an LTα-dependent manner upon BMT. (A) Experimental setup: WT CD45. 1:WT and WT CD45. 1:LTα$^{-/-}$ chimeras were treated with GST or RANKL-GST proteins at d2, d4 and d6 after BMT and TEC regeneration and T-cell reconstitution were analyzed at d21 after BMT. (B) Expression level of LTα in thymic LTi cells (C) Thymic sections from WT CD45.1:WT and WT CD45.1:LTα$^{-/-}$ mice treated with GST and RANKL at d2, d4 and d6 after BMT were stained for the expression of K14 at d21 pBMT. The histogram shows quantifications of medullary areas. m and c denote the medulla and the cortex, respectively. Twenty sections were quantified for each condition; Scale-bar: 100 μm. P-values were obtained by Student's t test. (D-E) Numbers of total TECs, cTECs and mTECs (D) and flow cytometry profiles of Aire$^+$ mTECs (E). (F) Expression of mRNAs coding for TRAs (SP1 and SP2) in thymic stromal cells analyzed by qPCR.

FIG. 3: Administration of risedronate in RANKL-treated mice prevents bone resorption without interfering with the beneficial effects of RANKL on thymic regeneration upon BMT. (A) TRAP staining of femur epiphysis and metaphysis analyzed at d21 pBMT from mice injected with GST, RANKL or RANKL+risedronate. 21, 12 and 24 sections were quantified for GST, RANKL and RANKL+risedronate conditions, respectively. Scale bar, 1 mm. B: bone; BM: bone marrow. (B-E) Numbers of total TECs, cTECs, mTECs (B), TEPC-enriched cells (C), total thymocytes and T-cell subsets (D) and ETPs (E) were analyzed at d21 in the thymus of GST, RANKL and RANKL+Risodronate-treated mice. Data are pooled of 2 independent experiments (n=3 mice per group). P-values were obtained by Student's t test.

FIG. 4. Beneficial effects mediated by RANKL treatment on thymic regeneration upon BMT also require LTα expression in aged mice. (A-B) Numbers of total TECs, cTECs, mTECs (A) and TEPC-enriched cells (B) were analyzed at d21 upon BMT in the thymus from WT CD45.1:WT and WT CD45.1:LTα$^{-/-}$ chimeras of 6-8 months of age treated with GST or RANKL proteins. (C-D) Numbers of total thymic cells, T-cell subsets (C) and ETPs (D) of CD45.1 origin. Data are pooled of 2 experiments (n=3 mice per group). P-values were obtained by Student's t test.

FIG. 5: In vivo administration of RANKL shows benefits to reverse the effects of aging on thymic involution. (A) Representative pictures of thymus from WT mice of 12 months of age at d21 after administration of GST or RANKL proteins during three consecutive days. (B-E) Numbers of total TECs, cTECs, mTECs (B), TEPC-enriched cells (C), total thymic cells and T-cell subsets (DN, DP, CD4$^+$ SP and CD8$^+$ SP) (D) and ETPs (E) were analyzed at d21 in the thymus from untreated WT mice of 6 weeks of age or of 12 months of aged treated with GST or RANKL-GST during three consecutive days. Data are pooled of 4 independent experiments (n=3 mice per group). P-values were obtained by Student's t test.

Figure 6:
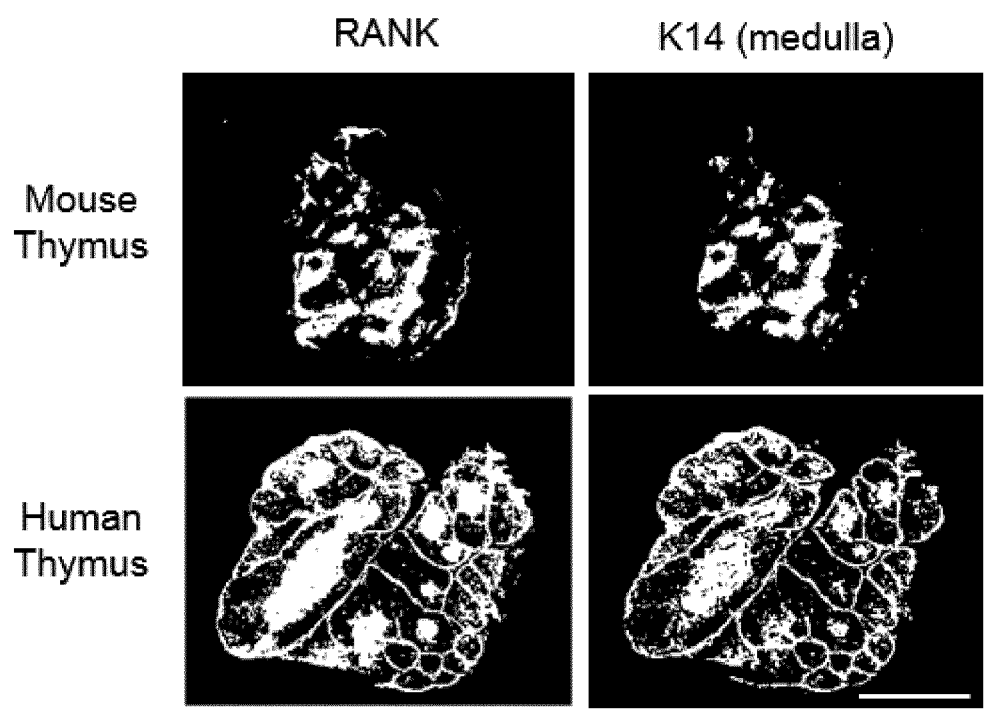

FIG. 6: RANK is mainly expressed in the thymic medulla both in mouse and human. Mouse and human thymic sections were stained with anti-RANK (green) and anti-K14 (red) antibodies and counterstained with DAPI (blue). m and c denotes the medulla and cortex, respectively. Scale bar, 5 mm.

EXAMPLE

Material & Methods

Human Sample

Human thymic fragments were obtained from normal male and female patients (3 months to 15 years old) during cardiovascular surgery at the Necker Hospital (Paris, France). All tissue samples were fast-frozen in liquid nitrogen within 30 minutes of their excision from patients.

Mice

CD45.1 and CD45.2 WT (Janvier), CD45.2 LTα$^{-/-}$ (34), Rag2$^{-/-}$ (Shinkai Y et al. Cell. 1992. PMID:1547487), ZAP-70$^{-/-}$ (Kadlecek T A et al. J Immunol. 1998. PMID: 9794398) and Rorc$^{GFP/GFP}$ knock-in (58) mice were on B6 background and maintained under specific pathogen-free conditions at the CIML (France). Chimeras were generated at 6-8 weeks or 6-8 months of age. WT mice of 12 months of age were used to analyze the effects of RANKL treatment on thymic involution.

Thymic Damage and BM Chimeras

TBI was performed with a Cs-137 γ-radiation source. Sublethal-TBI (SL-TBI) was performed with 500 rads with no hematopoietic rescue and lethal-TBI (L-TBI) with 2 doses of 500 rads. For the generation of chimeras, 10$^7$ BM cells of CD45.1 origin were injected i.v. into lethally irradiated (2×500 rads) CD45.2 WT or LTα$^{-/-}$ recipient mice.

RANKL and IL-22 Stimulations

The recombinant mouse RANKL-GST protein was produced as previously described (24). RANKL-GST (5 mg/kg) or GST (5 mg/kg) proteins were administrated i.v. daily during three days after SL-TBI or at day 2, 4 and 6 after BMT. Unmanipulated WT mice of 9-12 months of age were administrated i.v. with GST (5 mg/kg) or RANKL-GST (5 mg/kg) proteins during three consecutive days. Recombinant mouse IL-22 protein (200 μg/kg; R&D Systems) was administrated i.v. at days 2, 4, and 6 after BMT in combination or not with RANKL-GST protein.

RANKL Neutralization Experiments

Endotoxin anf azide-Free (LEAF) neutralizing anti-RANKL antibody (7.5 mg/kg; IK22/5; BioLegend) or purified Rat IgG2a, κ isotype control (7.5 mg/kg; RTK2758; BioLegend) were administrated i.v. during three days after SL-TBI.

Risedronate Treatment

WT mice were lethally irradiated, BM transplanted at day 0 and treated i.p. with risedronate (30 μg/kg; Sigma Aldrich) at day-2, −1, 0, 2, 4 and 6 before and after BMT. These mice were co-treated i.v. with GST or RANKL-GST proteins (5 mg/kg) at day 2, 4 and 6 after BMT.

TRAP Staining

Mouse femurs fixed in 4% paraformaldehyde during 48 h were decalcified with 10% EDTA, pH 7.5 during two weeks. 5 μm sections were deparaffinized and stained for TRAP activity (Sigma Aldrich) according to the manufacturer's instructions. Sections were counterstained with hematoxylin and images were quantified with ImageJ software.

TEC Isolation

TECs were isolated as previously described (29) by enzymatic digestion with collagenase D and DNase I (Roche) and depletion of hematopoietic cells using anti-CD45 magnetic beads and AutoMACS (Miltenyi Biotec).

Flow Cytometry

CD4 (RM4.5), CD8α (53-6.7), CD45.1 (A20), LTα (AF.B3), IL-7Rα (SB/199), CD80 (16-10A1), Ly51 (BP-1), I-Ab (AF6-120.1), CD45 (30-F11), CD44 (IM7) and Sca-1 (D7) antibodies were from BD. CD25 (PC61), RANK (R12-31), RANKL (IK22/5), CD3ε (145-2C11), lineage cocktail (145-2C11, RB6-8C5, M1/70, RA3-6B2, Ter-119), CD11c (N418), α6-integrin (GoH3) and CD31 (390) were from BioLegend. Foxp3 (FJK-16s), Ki-67 (SolA15), EpCAM (G8.8), LTβR (ebio3C8), Aire (5H12), RORγt (B2D), CD117 (2B8) and PDGFRα (APA5) were from eBioscience. FITC-conjugated UEA-1 was from Vector Laboratories. For RANKL and LTα detection, cells were incubated for 3 h with Brefeldin A (Biosciences). Foxp3 and Ki-67 intracellular stainings were performed with the Foxp3 staining kit (eBioscience). Aire, LTα, RANKL and RORγt intracellular stainings were performed with BD Cytofix/Cytoperm and Perm/Wash buffers. For staining with LTβR-Fc, cells were incubated with LTβR-Fc (RnD systems) at 1 μg/$10^6$ cells for 45 min on ice. LTβR-Fc staining was visualized using a Alexa Fluor 488-conjugated donkey anti-human IgG F(ab')$_2$ fragment (Jackson ImmunoResearch). Flow cytometry analysis was performed with a FACSCanto II (BD) and data were analyzed with FlowJo software.

Quantitative RT-PCR

Total RNA was prepared with TRIzol (Invitrogen). cDNAs was synthesized with oligo(dT) using Superscript II reverse transcriptase (Invitrogen). qPCR was performed with the ABI 7500 fast real-time PCR system (Applied Biosystem) and SYBR Premix Ex Taq master mix (Takara).

Immunofluorescence Staining

Frozen thymic sections were stained with Alexa Fluor 488-conjugated anti-Aire (5H12, ebioscience) and anti-keratin 14 (AF64, Covance Research) revealed with Cy3-conjugated anti-rabbit (Invitrogen). Frozen mouse and human thymic sections were stained with anti-RANK antibodies (R12-31, BioLegend for mouse detection; 80707, RnD systems for human detection) revealed with Cy3-conjugated goat anti-rat IgG (BioLegend) and with Alexa Fluor 488-conjugated donkey anti-mouse (Thermofischer) for mouse and human staining, respectively. Sections were counterstained with 1 μg/ml DAPI as previously described (59). Images were acquired with a LSM 780 Leica SP5x confocal microscope and quantified with ImageJ software.

Statistical Analysis

Statistical significance was assessed with GraphPad Prism 6 software using Student's t test or Anova on multiple variable analyses *, $P<0.05$; , $P<0.01$; *, $P<0.001$, ****, $P<0.0001$. Correlations were calculated using the nonparametric Spearman correlation test. Error bars represent mean±SEM.

Study Approval

Experiments were performed in accordance with the animal care guidelines of the European Union and French laws. All animal procedures were approved by and performed with in accordance with guidelines of the Centre d'Immunologie de Marseille-Luminy (CIML).

RESULTS

RANKL is upregulated during the early phase of thymic regeneration Because at steady state RANKL has been reported as a potent regulator of mTEC differentiation (25, 27, 31), we investigated whether this cytokine plays a role in thymic regeneration. To this, we first analyzed RANKL expression in the thymus at day 3 after SL-TBI (d3 SL-TBI) and found that RANKL was strongly upregulated in CD45$^+$ hematopoietic cells compared to untreated (UT) WT mice. Among hematopoietic cells, LTi cells, identified as CD4$^+$ CD3$^-$IL-7Rα$^+$ RORγt$^+$, and CD4$^+$ SP cells were clearly the main producers of RANKL, which was upregulated in a radiation dose-dependent manner. To definitively confirm the cellular source of RANKL, we analyzed the thymus from Rorc$^{-/-}$ mice, defective in LTi cells (35). Under physiological conditions, the thymus from Rorc$^{-/-}$ mice showed similar levels of RANKL mRNA compared to WT mice. In contrast, at d3 SL-TBI, while the expression of RANKL was strongly upregulated in the WT thymus, thymus from Rorc$^{-/-}$ mice failed to increase RANKL, suggesting that LTi cells are required for RANKL upregulation after thymic damage. However, since Rorc$^{-/-}$ mice show reduced numbers of DP and CD4+ SP cells, we also analyzed RANKL expression in the thymus of UT in ZAP-70$^{-/-}$ mice, lacking SP cells, to determine the contribution of CD4+ SP cells in RANKL expression. Strikingly, thymus from ZAP-70$^{-/-}$ mice failed to increase RANKL after SL-TBI, indicating that CD4$^+$ SP cells constitute the major source of RANKL. Furthermore, RANKL expression in the thymus of Rag2−/− mice, lacking both DP and CD4$^+$ SP but having normal numbers of LTi cells, is upregulated after SL-TBI but to a lesser extent than in WT thymus at d3 SL-TBI. These data thus indicate that RANKL is mainly produced by CD4$^+$ SP and LTi cells after irradiation. RANKL was upregulated in these two cell-types until day 10 after SL-TBI with no hematopoietic rescue, implying that RANKL upregulation occurs in the early phase of thymic regeneration.

The Administration of RANKL Boosts TEC Regeneration Upon Thymic Damage

The aforementioned data strongly suggest that RANKL could play a role in thymic regeneration after irradiation. To confirm this assumption, WT mice were treated with a neutralizing anti-RANKL antibody (IK22/5) during three days after SL-TBI. PBS- and isotype antibody-treated mice were used as controls. The administration of neutralizing anti-RANKL antibody led to an impaired TEC regeneration illustrating by a 2.5-fold decrease in numbers of total TECs (EpCAM$^+$), cTECs (EpCAM$^+$UEA-1$^-$Ly51$^+$) and mTECs (EpCAM$^+$UEA-1$^+$Ly51$^-$) compared to controls. In a therapeutic perspective, we next investigated whether conversely the ex vivo administration of RANKL protein shows beneficial effects on TEC regeneration. WT mice were treated with RANKL-GST protein during three days after SL-TBI. PBS- and GST-treated mice were used as controls. Remarkably, RANKL-treated mice showed a two-fold increase in numbers of total TECs, cTECs and mTECs compared to controls (FIG. 1). RANKL treatment also enhanced CD80hiAire−, CD80hiAire+ mTECs and several TEC subsets based on MHCII expression level (36): mTEC$^{hi}$ (MHCII$^{hi}$UEA-1$^+$), TEC$^{lo}$ (MHCII$^{lo}$UEA-1$^{lo}$), and mTEC$^{lo}$ (MHCII$^{lo}$UEA-1$^+$). Interestingly, a TEC population described to be enriched in TEPCs defined as α6-integrin$^{hi}$Sca-1$^{hi}$MHCII$^{lo}$ in the TEC$^{lo}$ subset (36) was also increased.

To gain mechanistic insights into the mode of action of RANKL, we analyzed the proliferation status of cTECs, mTECs and TEPCs. Numbers of Ki-67$^+$ cells in these three populations were increased in RANKL-treated mice. Purified mTECs showed reduced expression of Bax, Bid and Bak pro-apoptotic genes and cTECs reduced expression of Bax and increased expression of the Bcl-xl anti-apoptotic gene. Furthermore, the density of medullary Aire$^+$ cells and the expression of Aire and Aire-dependent TRAs were enhanced. Interestingly, we also found that RANKL stimulated in cTECs the expression of Selp, ICAM-1 and CCL21, implicated in thymus homing of lymphoid progenitors. Altogether, these data show that RANKL administration boosts TEC proliferation, survival and differentiation and thus enhances TEC regeneration after thymic damage.

RANKL Administration Induces LTα Upregulation in LTi Cells After TBI

We next investigated the underlying mechanism(s) of RANKL treatment. Interestingly, we found that irradiation led to the upregulation of RANKL cognate receptor, RANK on LTi cells. Thus, a possible mechanism is that RANKL acts on this cell-type. Furthermore, during embryogenesis, in vitro experiments have shown that RANKL induces LTα in peripheral LTi cells (37). To investigate whether RANKL regulates in vivo LTα in thymic LTi cells after irradiation, WT mice were treated with RANKL-GST or GST proteins for three days after SL-TBI. Thymic LTi cells from RANKL-treated mice upregulated LTα compared to those from GST-treated mice. Conversely, the administration of a neutralizing anti-RANKL antibody inhibited LTα upregulation in LTi cells that was expressed at similar level than that observed in non-irradiated WT mice (UT). Moreover, in vitro stimulation with RANKL-GST also significantly stimulated LTα expression specifically in LTi cells while the addition of RANKL antagonist, RANK-Fc, fully blocked LTα induction, demonstrating the specificity of the treatment used. Consistently, LTα upregulation tightly correlated with that of RANKL during the course of BMT. Interestingly, both LTα and LTβ mRNAs were increased in the total thymus at d3 SL-TBI compared to UT WT mice. LTα was specifically induced in hematopoietic cells and LTi were the main producers of LTα and LTI3. We hypothesized that LTα could be expressed as a membrane anchored LTα1β2 heterocomplex, which only binds to LTβR (38). We used a soluble LTβR-Fc fusion protein, which detects the two LTβR ligands, LTαβ2 and LIGHT. In contrast to LTα and LTβ, LIGHT was slightly expressed and not upregulated after thymic injury, indicating that LTβR-Fc staining detects only LTαβ2 in LTi cells, which is upregulated in a radiation dose-dependent manner. Finally after BMT, LTα protein was selectively upregulated in LTi cells from recipient and not from donor origin until day 6 after thymic injury, showing the importance of the host LTi cells in LTα production. These data thus show that RANKL treatment induces LTα expression in LTi cells early after thymic injury.

LTα is Critical for TEC Regeneration and De Novo Thymopoïesis During the Course of BMT We next addressed whether LTα upregulation in response to RANKL treatment after TBI is involved in thymic regeneration. In line with this assumption, total TECs, cTECs and mTECs but also TEPC-enriched cells upregulated LTβR at d3 SL-TBI. While at steady state, LTα$^{-/-}$ mice, in which the expression of LTαβ2 is fully lost, did not show any defect in thymocytes and TEC subsets (32, 34), numbers of cTECs, mTECs and mTEC subsets (CD80$^{lo}$Aire$^-$, CD80$^{hi}$Aire$^-$ and CD80$^{hi}$Aire$^+$) as well as the density of Aire$^+$ cells were dramatically reduced at d3 SL-TBI. Of note, no significant defect neither in CD45$^-$PDGFRα$^+$ fibroblasts nor in thymic LTi cells was observed in LTα$^{-/-}$ mice at d3 SL-TBI. To definitively address the role of LTα during thymic recovery after BMT, lethally irradiated CD45.2 WT or LTα$^{-/-}$ recipients were reconstituted with CD45.1 congenic BM cells (WT CD45.1:WT or WT CD45.1:LTα$^{-/-}$ mice) and TEC numbers were analyzed at day 10, 21 and 65 after BMT. We observed reduced numbers of total TECs, cTECs and mTECs as well as mTEC subsets in WT CD45.1:LTα$^{-/-}$ mice compared to WT CD45.1:WT controls at all time points analyzed. Moreover, cTEC$^{hi}$, mTEC$^{hi}$, TEC$^{lo}$, mTEC$^{lo}$ and TEPC-enriched cells were also reduced. Importantly, total TECs, cTECs, mTECs and TEPCs were less proliferative. A reduced density of medullary Aire$^+$cells was still detectable at d65 after BMT and consequently, the expression of Aire-dependent TRAs (SP1 and SP2) was strongly affected. The expression of an Aire-independent TRA (casein β) and Fezf2 as well as its target genes (Apoc3, Fabp9 and Resp18) (5) were also reduced. These data thus reveal that LTα is critical for TEC regeneration including TEPCs during the course of BMT.

In line with these thymic environmental defects, thymocytes were reduced from double-negative (DN) to SP stage after BMT in WT CD45.1:LTα$^{-/-}$ mice. Consequently, numbers of peripheral CD4$^+$ and CD8$^+$ T cells as well as CD4$^+$ Foxp3$^+$ regulatory T cells (Tregs) from CD45.1 donor origin were reduced in the blood and spleen of WT CD45.1:LTα$^{-/-}$ mice from d21 to d100 after BMT.

Since de novo thymopoïesis was impaired from DN1 stage in WT CD45.1:LTα$^{-/-}$ mice, we analyzed early T-lineage progenitors (ETPs; CD4$^-$CD8$^-$CD44$^+$ CD25$^-$Lin$^-$ CD117$^+$). Whereas numbers of ETPs were normal in LTα$^{-/-}$ thymus at steady state, ETPs from CD45.1 donor origin were reduced in WT CD45.1:LTα$^{-/-}$ chimeras until two months after BMT. This defect was not attributable to impaired hematopoietic progenitors because normal numbers of prethymic progenitors were observed in the BM of these mice. We hypothesized that reduced ETPs could be due to a reduced homing capacity of circulating T-cell progenitors. Thymus homing is controlled by a multistep adhesion cascade initiated by P-selectin slowing down T-cell progenitors and allowing them to respond to CCL25, CCL21/19 gradients and to engage with ICAM-1 and VCAM-1 expressed by the thymic stroma, leading to a firm arrest (39, 42). Strikingly, we found that purified CD31+ endothelial cells from WT CD45.1:LTα$^{-/-}$ mice showed a reduced expression of adhesion molecules such as ICAM-1, VCAM-1 and P-selectin at d21 after BMT. Furthermore, purified EpCAM+ TECs in these mice also showed a reduced expression of CCL19 and CCL21. Endothelial cells and TECs were thus defective in key molecules involved in thymus homing in absence of LTα during BMT. To firmly demonstrate that thymus homing of T-cell progenitors was altered in LTα$^{-/-}$ mice, short-term homing assays were performed by injecting CD45.1 congenic BM cells into irradiated WT and LTα$^{-/-}$ recipients. LTα$^{-/-}$ thymi imported three-fold less ETPs than WT thymi after thymic injury.

It is noteworthy that the effects of LTα on TEC and T-cell recovery were independent of those mediated by IL-23-regulated IL-22 described to be involved in thymic regeneration (43) since LTα$^{-/-}$ mice exhibited similar production of these two cytokines after TBI. Of note, RANKL was expressed at normal level at d3 SL-TBI in LTα$^{-/-}$ mice, suggesting that LTα did not regulate RANKL. Altogether, these results reveal that RANKL-regulated LTα constitutes an indispensable pathway for thymic regeneration.

We next investigated the respective efficiency of IL-22 and RANKL in thymic recovery during BMT. BM-transplanted mice were treated with IL-22 or RANKL at d2, d4, and d6 after BMT and thymic regeneration was analyzed at d21 (data not shown). We found that IL-22 and RANKL administrated alone increased similarly numbers of developing T cells including ETPs and ameliorated peripheral T-cell reconstitution. Importantly, IL-22 alone increased only numbers of CD80$^{hi}$ mTECs, whereas RANKL alone enhanced numbers of all TEC subsets including cTECs and mTECs from the immature CD80$^{lo}$ to the mature CD80$^{hi}$ stage. The numbers of cTEC$^{hi}$, mTEC$^{hi}$, TEC$^{lo}$, mTEC$^{lo}$, and TEPC-enriched cells were also increased only in RANKL-treated mice. Thus, RANKL and IL-22 do not exhibit the same effects on TEC regeneration with a preferential effect for IL-22 on only mTEC$^{hi}$ and a more large effect for RANKL on all TEC subsets. These data thus indicate that RANKL shows a superior ability than IL-22 to recover TECs after BMT.

Figure 2A:
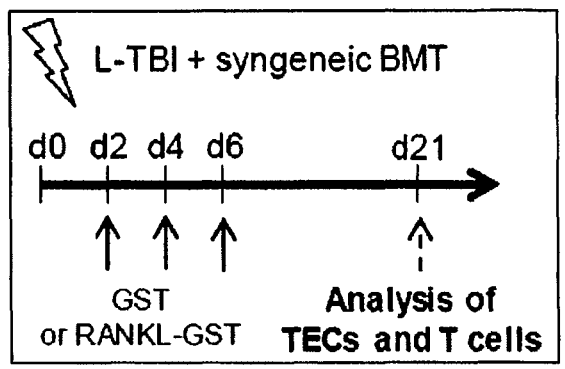
Figure 2B:
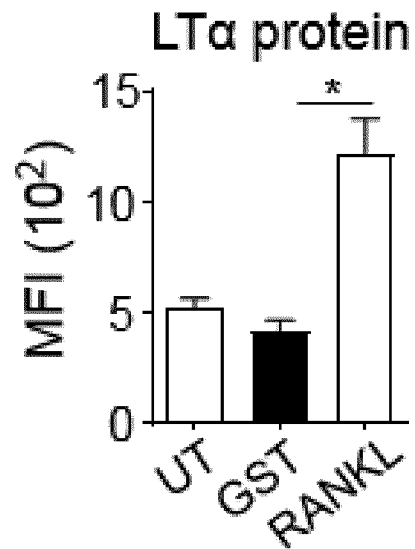
Figure 2C:
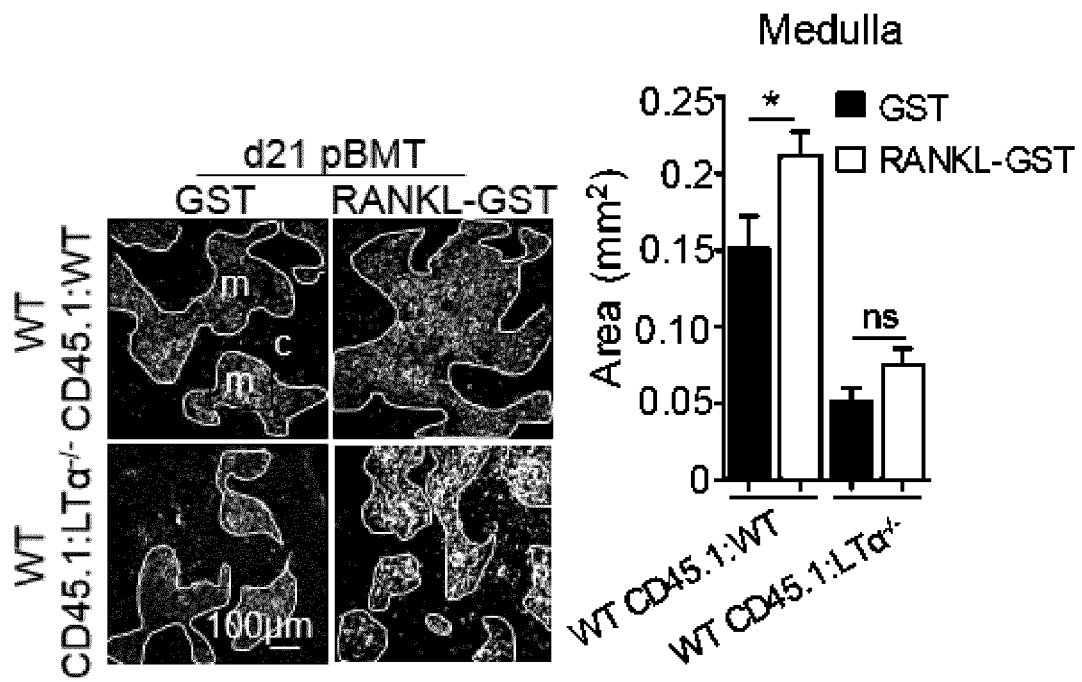
Figure 2D:
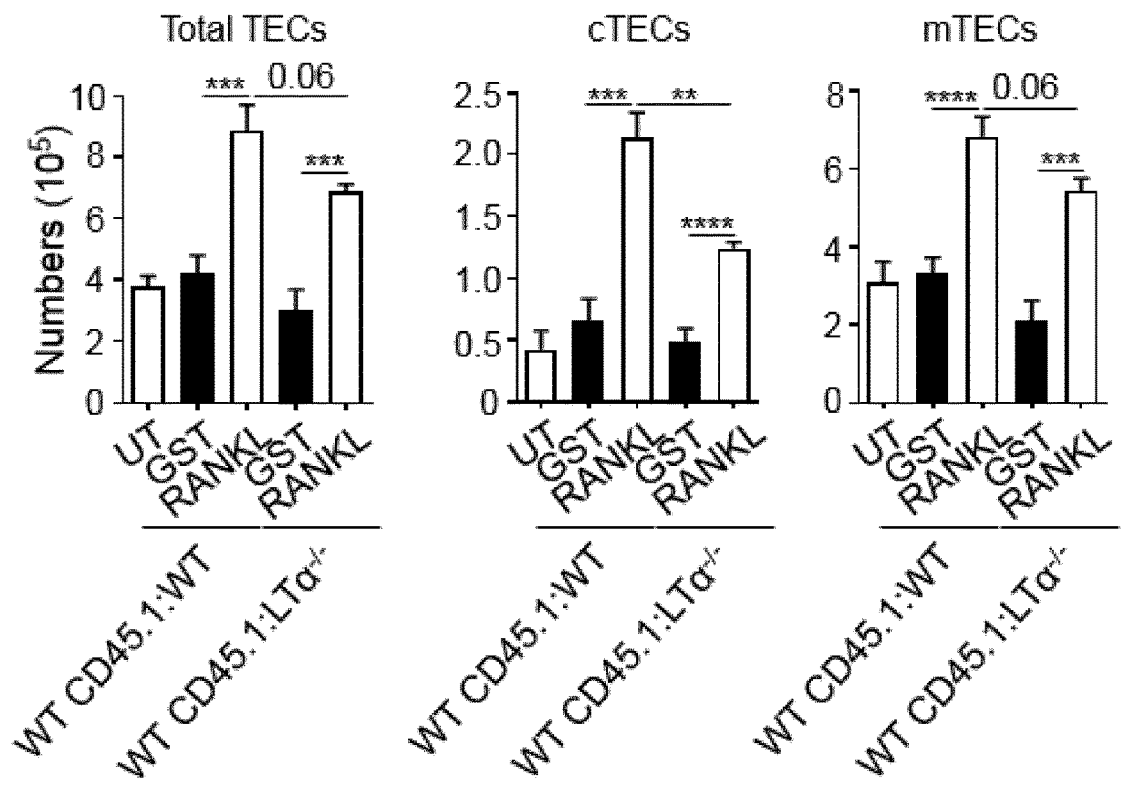
Figure 2E:
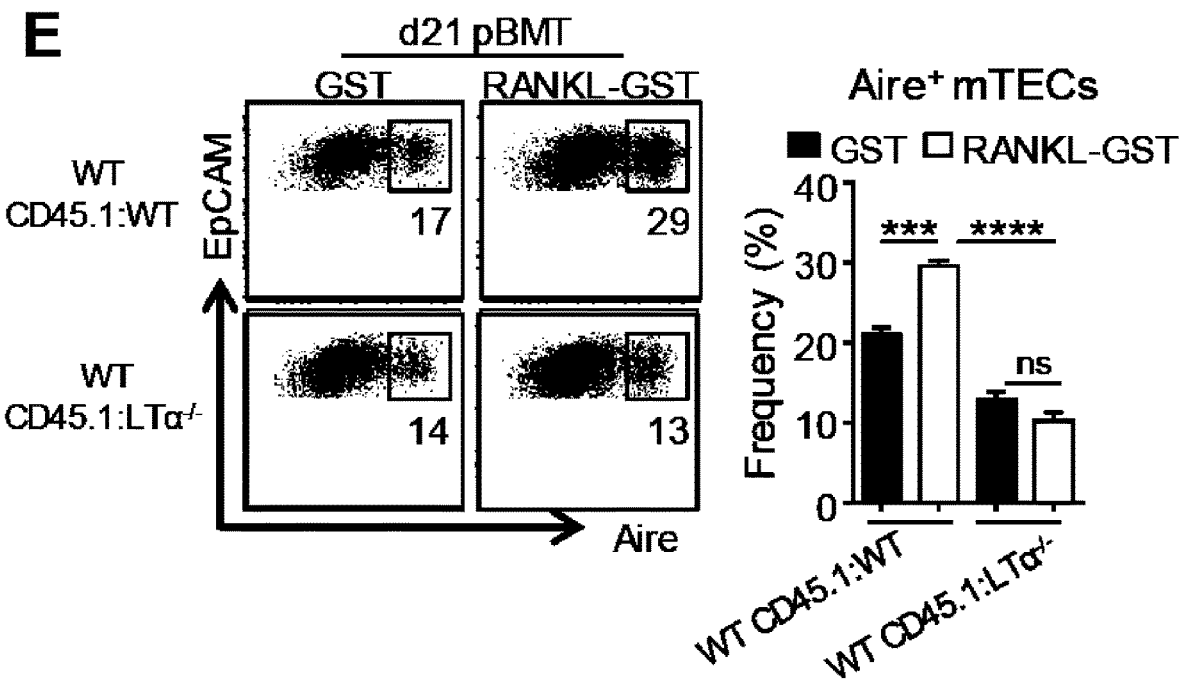
Figure 2F:
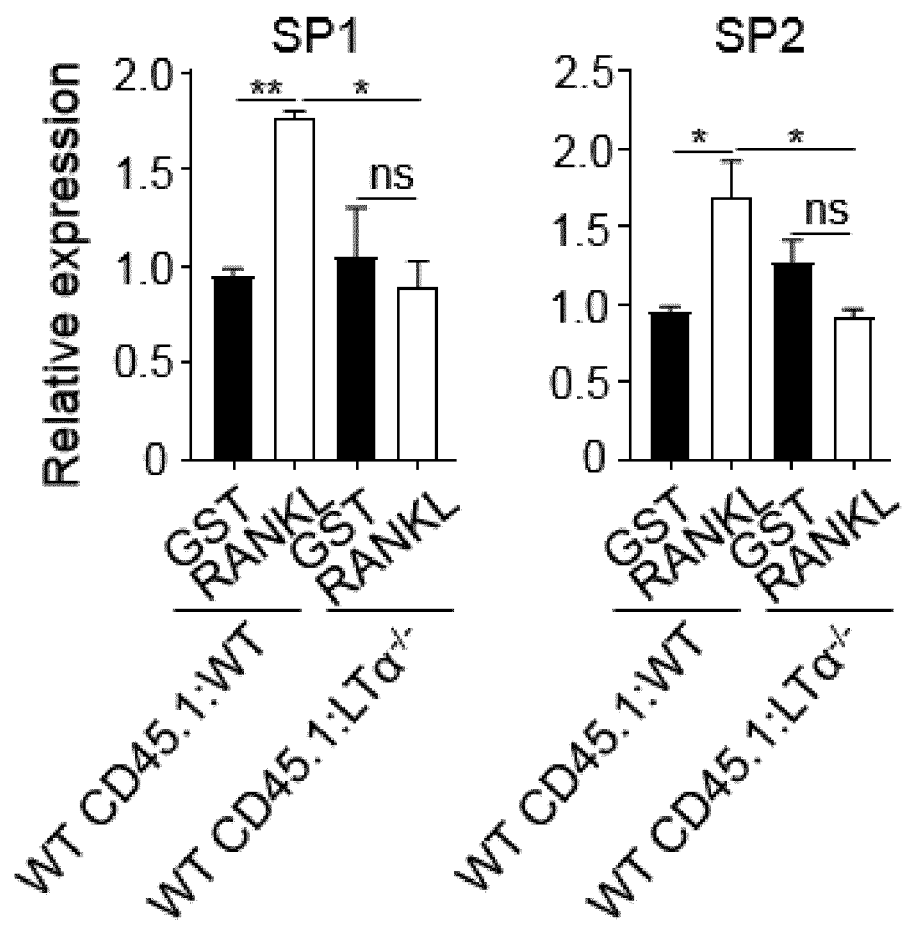

RANKL Administration Enhances Thymic Regeneration Upon BMT in an LTα-Dependent Manner Since RANKL treatment improves TEC regeneration upon SL-TBI (FIG. 1), we next evaluated whether RANKL boosts thymic recovery during the course of BMT. WT mice transplanted with CD45.1 BM cells were treated with RANKL-GST or GST at d2, d4 and d6 after BMT and thymic regeneration was analyzed at d21 (FIG. 2A) and d65 after BMT. In these experiments, as observed at d3 SL-TBI, RANKL treatment also upregulated LTα in LTi cells, which is still detectable at d21 pBMT (FIG. 2B). RANKL-treated WT CD45.1:WT mice showed increased medullary areas, numbers of TEC subsets, Aire$^+$ mTEC frequency and Aire-dependent TRAs compared to GST-treated mice (FIG. 2C-F). RANKL also increased numbers of endothelial cells. Because we found that RANKL regulates LTα, we next investigated whether these beneficial effects on TECs mediated by RANKL require LTα expression. The administration of RANKL in WT CD45.1:LTα$^{-/-}$ mice increased TEC numbers but to a lesser extent compared to RANKL-treated WT CD45.1:WT mice (FIG. 2D). In contrast, RANKL treatment in these mice did not enhance neither Aire$^+$ mTEC frequency nor Aire-dependent TRAs, indicating that LTα is critical for regeneration of Aire$^+$ mTECs (FIG. 2E-F).

Interestingly, RANKL in WT CD45.1:WT chimeras substantially increased numbers of total donor cells and thymocytes of CD45.1 origin from ETP to SP stages at d21 and d65 upon BMT. In contrast, RANKL administration in WT CD45.1:LTα$^{-/-}$ mice had a poor effect on de novo thymopoïesis. To decipher the mode of action of RANKL on T-cell reconstitution, we performed short-term homing assays in irradiated WT and LTα$^{-/-}$ mice treated with GST or RANKL. Strikingly, the receptivity capacity of circulating progenitors was substantially enhanced in RANKL-treated WT CD45.1:WT mice compared to GST-treated controls. Importantly, this was not due to increased numbers of prethymic progenitors in the BM upon RANKL treatment. In contrast, RANKL had no effect on ETP homing in WT CD45.1:LTα$^{-/-}$ mice. Consequently, RANKL treatment increased peripheral T-cell reconstitution only in WT CD45.1:WT mice after BMT. Altogether, these data demonstrate that LTα is critical for optimal effects of RANKL administration on TEC regeneration, thymus homing of lymphoid progenitors and T-cell reconstitution upon BMT.

Figure 3A:
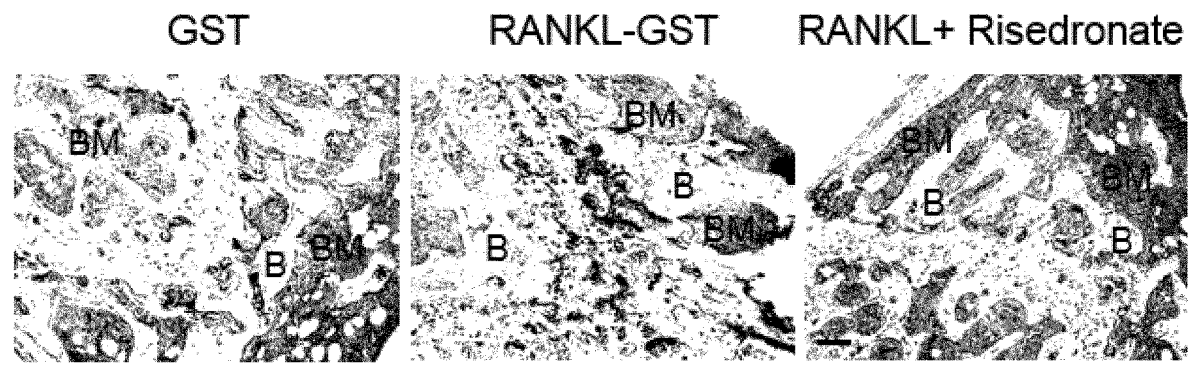
Figure 3A:
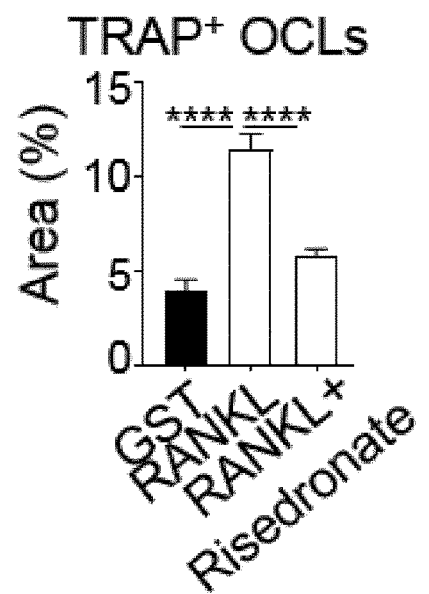
Figure 3B:
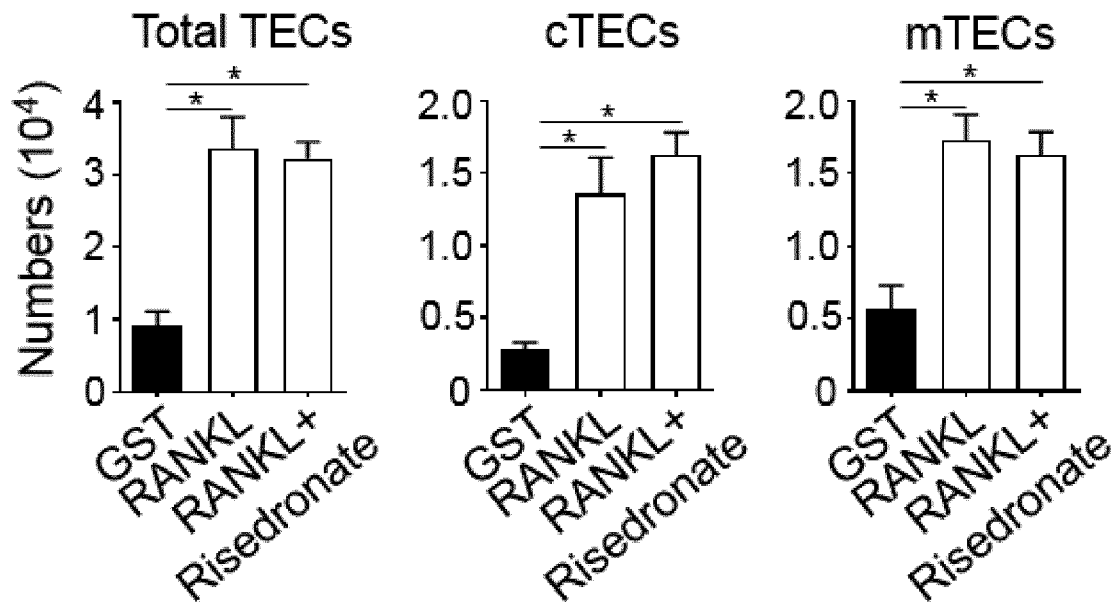
Figure 3C:
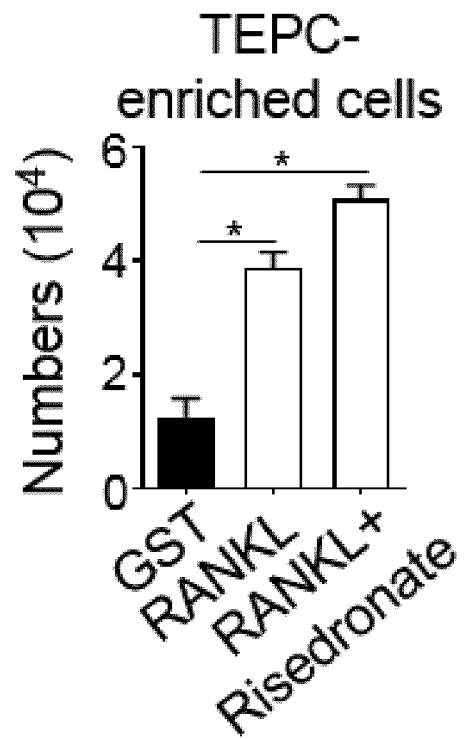
Figure 3D:
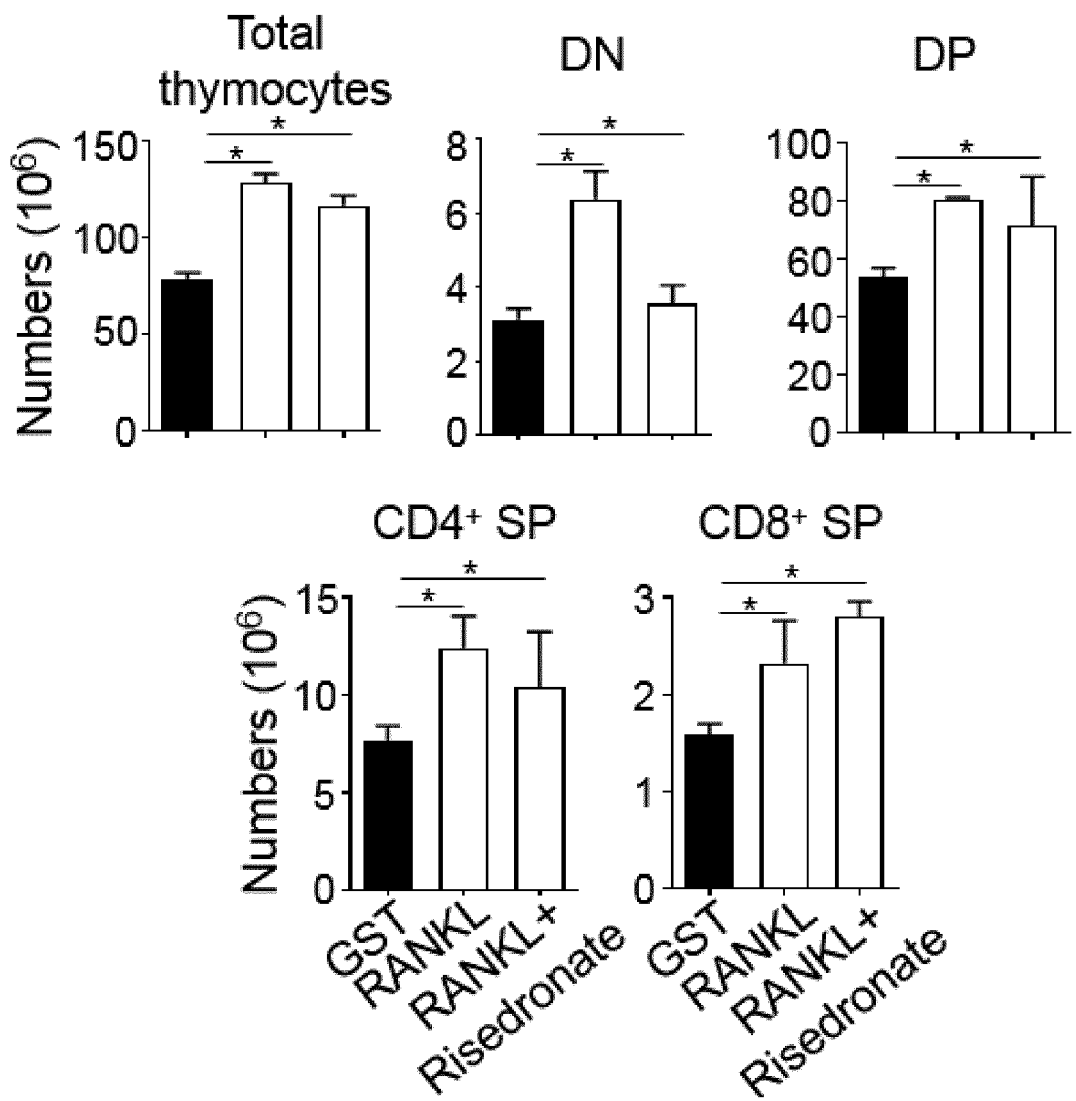
Figure 3E:
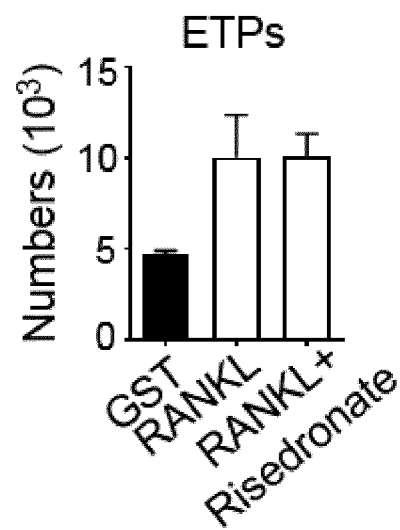

Bisphosphonate Treatment Protects From One Resorption Without Affecting RANKL-Improved Thymic Regeneration Given that RANKL administration upon BMT increased primitive progenitors in the BM, which correlated with the development of active osteoclasts (Kollet O, Dar A, Shivtiel S, Kalinkovich A, Lapid K, Sztainberg Y, Tesio M, Samstein R M, Goichberg P, Spiegel A, Elson A, Lapidot T. (2006) Osteoclasts degrade endosteal components and promote mobilization of hematopoietic progenitor cells. Nat Med. 12(6):657-64), we have investigated whether combining RANKL with bisphosphonates, which is described to prevent bone resorption (Tomimori Y, Mori K, Koide M, Nakamichi Y, Ninomiya T, Udagawa N, Yasuda H. (2009) Evaluation of pharmaceuticals with a novel 50-hour animal model of bone loss. J Bone Miner Res. 2009 Jul. 24(7): 1194-205), protects from the development of osteoclasts without interfering with RANKL beneficial effects on thymic regeneration during BMT. The development of osteoclasts and thymic regeneration were analyzed in WT mice treated with GST and RANKL as well as in mice co-treated with risedronate and RANKL. Active osteoclasts were identified by expression of the phosphatase TRAP 21 days after BMT. The areas stained for TRAP$^+$ osteoclasts were increased in RANKL-treated mice compared to GST-treated mice (FIG. 3A). Strikingly, TRAP$^+$ areas in mice co-treated with risedronate and RANKL returned at the same level than in GST-treated mice. Importantly, this combined treatment did not impair TEC regeneration and T-cell reconstitution mediated by RANKL (FIG. 3B-F), indicating that risedronate can be used concomitantly with RANKL to protect from bone resorption.

Figure 4A:
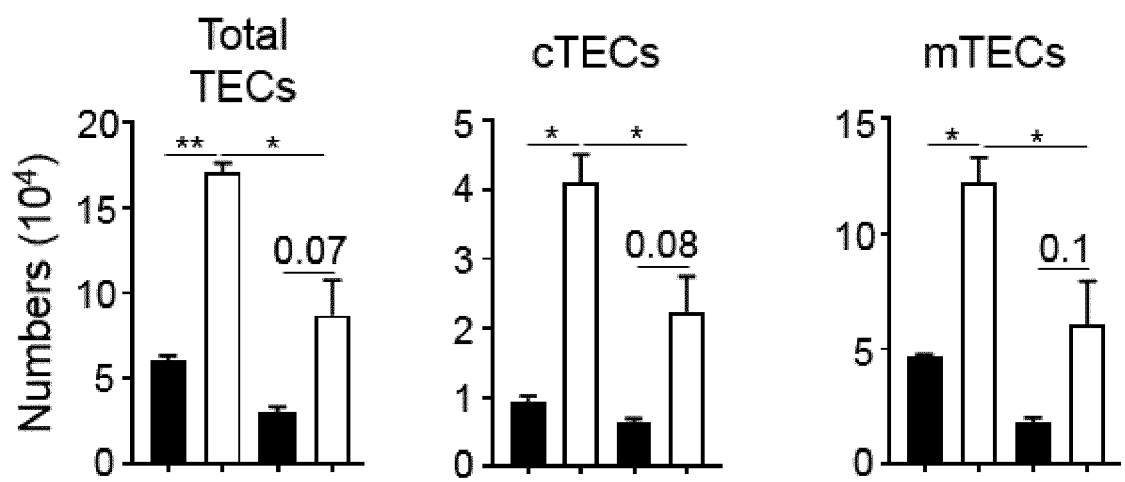
Figure 4B:
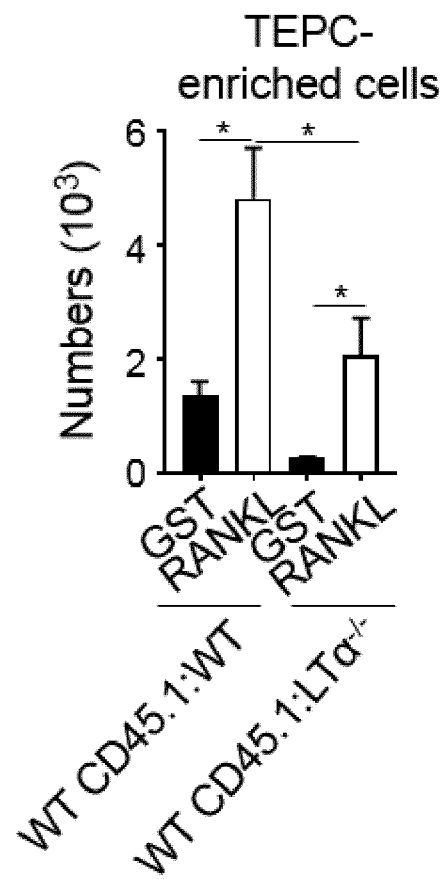
Figure 4C:
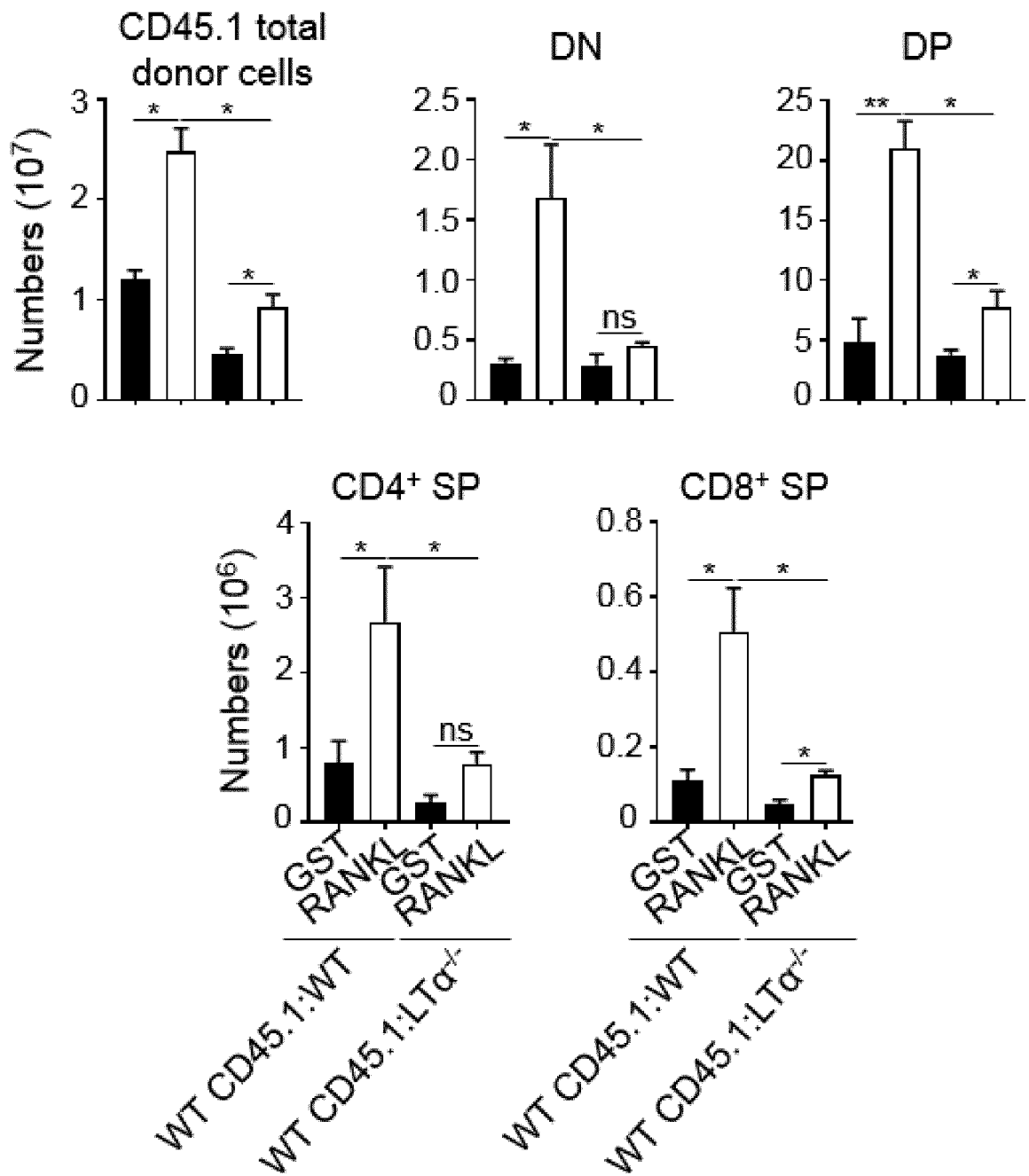
Figure 4D:
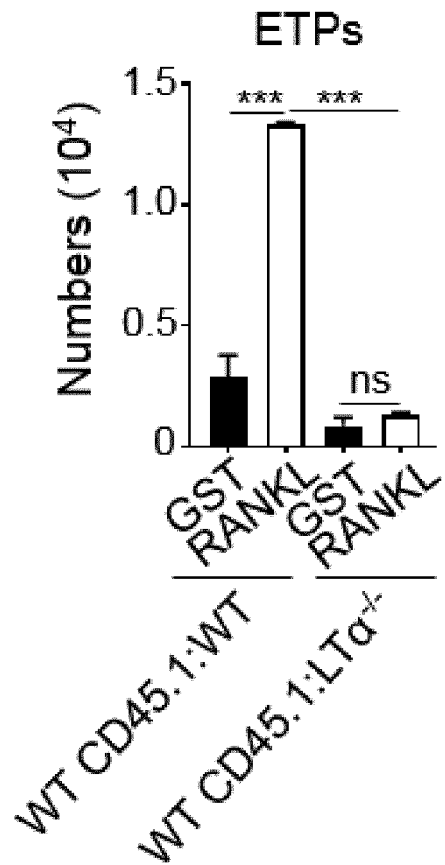

RANKL Treatment has Also Beneficial Effects on Thymic Recovery Upon BMT in Aged Individuals Because the recovery of T-cell functions upon BMT is known to be delayed and less efficient in elderly patients compared to young individuals (44), we finally investigated whether RANKL beneficial effects are persistent with age. To this, WT mice of 6-8 months, in which early thymic involution is characterized by a decline in TEC cellularity (45, 46), were subjected to the same treatment described in FIG. 2A. We found that RANKL increased numbers of cTECs, mTECs and TEPCs (FIG. 4A-B). All thymocytes including ETPs were also increased in these mice (FIG. 4C-D). Importantly, RANKL administration in WT CD45.1: LTα$^{-/-}$ chimeras did not improve significantly TEC cellularity compared to RANKL-treated WT CD45.1:WT mice (FIG. 4A-B). Moreover, RANKL treatment had only minor effects on de novo thymopoïesis in WT CD45.1:LTα$^{-/-}$ chimeras (FIG. 4C-D). Peripheral T-cell reconstitution was thus only enhanced in RANKL-treated WT CD45.1:WT mice. This set of data is consistent with the fact that LTi cells persisted with age and upregulated LTαβ2 after TBI in older mice. Furthermore, BM-transplanted LTα$^{-/-}$ mice of 6-8 months of age showed defective TEC regeneration, de novo thymopoiesis and peripheral T-cell reconstitution. Altogether, our data indicate that RANKL treatment boosts thymic recovery after BMT not only in young but also in older individuals in an LTα-dependent manner.

The Administration of RANKL Reverses the Effects of Thymic Involution

Figure 5A:
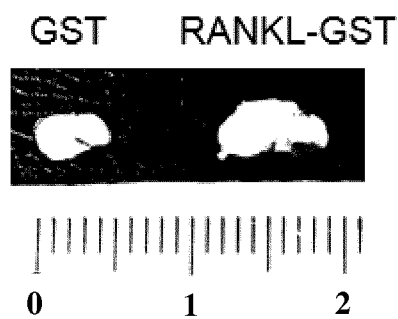
Figure 5B:
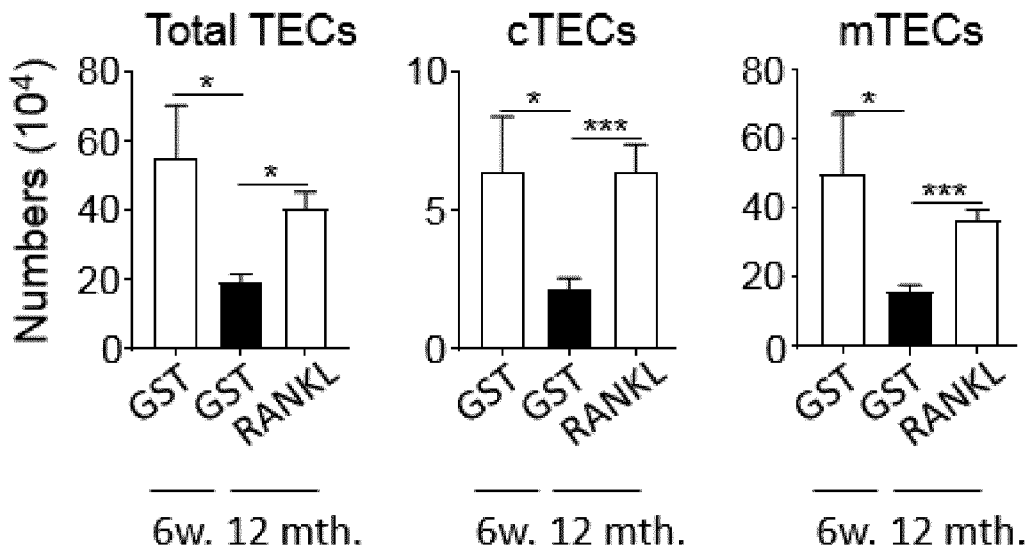
Figure 5C:
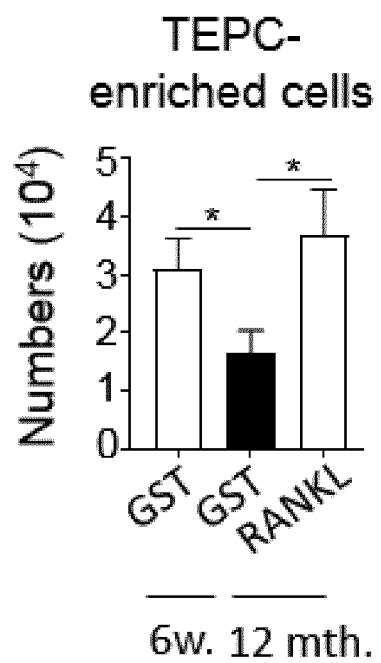
Figure 5D:
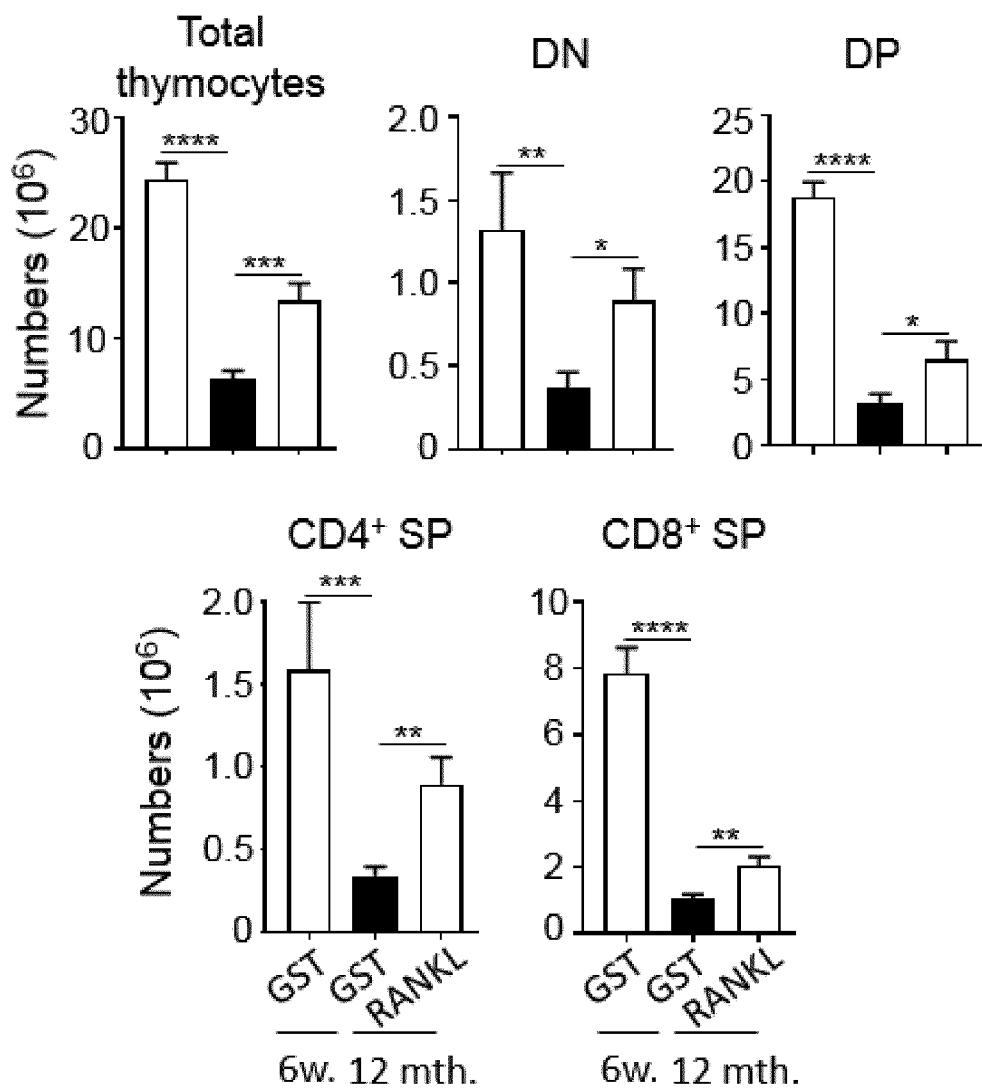
Figure 5E:
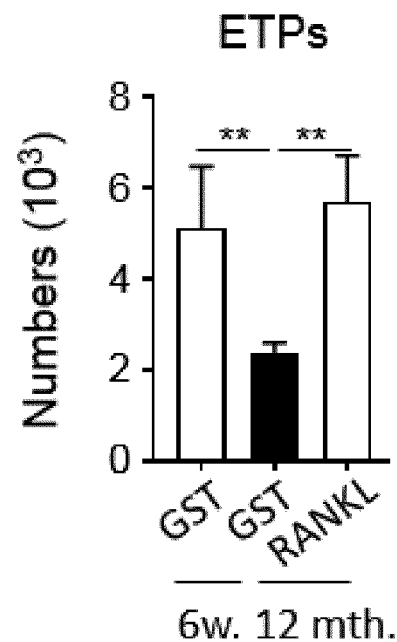

Age-associated thymic involution results in decreased TEC cellularity and T-cell development, which leads to increased morbidity and mortality in a numerous clinical settings. Importantly, the thymus shows compelling plastic properties and thus the effects of thymic involution can be therapeutically reversed. Since we found that RANKL improve thymic regeneration upon BMT in young and aged individuals, we hypothesized that this treatment could increase thymopoietic capacity at steady state in aged mice to ameliorate the effects of age-associated thymic involution. 12 months of age WT mice were treated with GST or RANKL-GST during three consecutive days and thymus composition was analyzed 21 days later. Strikingly, the thymus size was increased in RANKL-treated mice compared to GST-treated mice (FIG. 5A). Furthermore, numbers of total TECs, cTECs and mTECs as well as TEPC-enriched cells were substantially increased in these mice (FIG. 5B, C). T cell cellularity in RANKL-treated aged mice increased about 2.5 fold compared to GST controls (FIG. 5D,E). Importantly, although numbers of T-cell subsets in RANKL-treated aged mice did not recover to the same level than those observed in young mice, numbers of TECs and ETPs were barely similar to mice of 6 weeks of age. Finally, RANKL treatment in mice of 12 months of age increased peripheral T-cell reconstitution at a similar level than that observed in young mice (data not shown). Thus, these data show that RANKL partially reverses the effects of thymic involution.

The Expression of RANKL Receptor, RANK, is Conserved in the Thymic Medulla in Human To determine whether the administration of RANKL protein could be conceivable in human, we first compared the expression of its receptor, RANK, on mouse and human thymic sections. Similarly to the mouse thymus, RANK was mainly expressed in the thymic medulla in human (FIG. 6). These data suggest that thymic human cells should be able to respond to RANKL stimulation and thus that this treatment could have significant clinical impacts for improving thymus reconstitution during BMT as well as reversing the effects of age-associated thymic involution.

DISCUSSION

Pre-BMT conditioning induces severe damages on the thymic microenvironment, which results in delayed lymphocyte production. It is therefore of paramount clinical interest to discover new molecules that enhance thymic regeneration for an efficient recovery of the immune system (8, 11).

Our study demonstrates that the administration of RANKL substantially improves thymic recovery during BMT. We found that thymic LTi cells and CD4$^+$ SP cells, described to be radio-resistant (43) (Tomoo Ueno et al. J Exp Med, 2004), constitute the major source of RANKL. Administration of RANKL induces LT$\alpha$ expression specifically in LTi cells after injury. Furthermore, thymic LTi cells from recipient origin upregulated both RANKL and LT$\alpha$ during the early phase of BMT. Thus, these cells change their phenotype upon stress-induced thymic damage. Thymic LTi cells are thus likely in a "quiescent stage" at steady state and are activated after irradiation to repair the injured tissue. When considering that LTi cells expressing RANKL and LT$\alpha$ are involved in the organogenesis of lymph nodes (47), our data suggest that thymic LTi cells likely reactivate an embryonic program to repair the thymus after irradiation.

Interestingly, we found that RANKL administration after TBI boosts the regeneration of TEC subsets including TEPC-enriched cells. Conversely, the administration of a neutralizing anti-RANKL antibody leads to an impaired TEC regeneration. Furthermore, flow cytometry, histology and qPCR experiments indicated that RANKL administration also boosts the regeneration of Aire$^+$ mTECs. Importantly, RANKL treatment during the early phase of BMT enhances numbers of TECs, ETPs and thymocytes. We demonstrated that thymus homing of T-cell progenitors and T-cell output are improved. Notably, although mice were treated during the early phase of BMT, RANKL treatment had long-term beneficial effects detectable until two months after BMT on both TEC and T-cell compartments. Improved T-cell reconstitution can be explained by increased stromal niches linked to increased TEC cellularity but also to enhanced thymus homing of lymphoid progenitors, which is a critical step for ameliorating T-cell recovery (19, 21). The latter effect is likely mediated by increased expression of adhesion molecules and chemokines involved in this process. Nevertheless, we cannot exclude that the enhanced thymus homing by RANKL administration is also favored by increased vasculature, which is important for thymus homing. Thus, our data reveal that RANKL plays distinct roles in the thymus at steady state and during BMT.

We further found by in vitro and in vivo stimulations that RANKL induces LT$\alpha$ in LTi cells, which express its cognate receptor, RANK. Importantly, the administration of a neutralizing RANKL-antibody inhibits LT$\alpha$ upregulation in LTi cells, indicating that RANKL specifically controls LT$\alpha$ upregulation after SL-TBI. In contrast, LT$\alpha$ did not regulate RANKL, indicating that LT$\alpha$ acts downstream of RANKL. Whereas LT$\alpha$ is dispensable at steady state for TEC and T-cell cellularity, we found that LT$\alpha$ is critical for the recovery of thymic function. TEC subsets including TEPCs were severely reduced in LT$\alpha^{-/-}$-transplanted recipients from up to two months after BMT. Moreover, all thymocyte subsets as well as ETPs were also reduced in these mice likely due to defective thymus homing capacity. In accordance with our data, it has been recently reported that LT$\beta$R regulates VCAM-1 and ICAM-1 on endothelial cells, known to promote T-cell progenitor entry in the thymus (40, 49, 50). Consistently, we found that LT$\alpha$ expression is important for the expression of adhesion molecules and chemokines in stromal cells during BMT. Given that in the steady state thymus, LT$\alpha$ expressed by SP thymocytes, is involved in the regular thymic architecture (12, 33, 51, 52), our data show that LT$\alpha$ expressed by LTi cells after thymic injury plays distinct roles.

Furthermore, it has been described that IL-22 participates to thymus recovery (43). Our data reveal that RANKL-regulated LT$\alpha$ in LTi cells represents a distinct mechanism of that mediated by IL-22 in thymic regeneration and thus highlighting that this cell-type uses different mechanisms for thymic repair. Importantly, although IL-22 treatment during BMT enhances only mature CD80$^{hi}$ mTECs, our data demonstrate that RANKL treatment ameliorates the regeneration of not only CD80$^{hi}$ mTECs but also CD80$^{lo}$ mTECs and cTECs. The administration of RANKL boosts also the recovery of TEPCs, which are essential for the renewal of stromal niches after BMT. These results thus show that in contrast to IL-22, RANKL has large spectrum effects on TECs with a superior ability to regenerate these cell populations. Importantly, whereas IL-22 treatment had no more effect on thymopoïesis at d28 after BMT, RANKL administration boosts thymic regeneration until d65 after BMT. Thus, RANKL constitutes an innovative therapy to enhance thymic regeneration after BMT by acting on both TEC and T-cell reconstitution. One would expect that thymic regeneration during the course of BMT is also defective in RANKL$^{-/-}$ mice. Unfortunately, we were unable to test this hypothesis since RANKL$^{-/-}$ mice show severe growth retardations (53) and exhibit a drastic reduction in mTECs (27).

In addition, the administration of fibroblast growth factor 7 (Fgf-7) before BMT has been shown to protect TECs and ameliorates the thymopoïetic capacity (Min D, Taylor P A, Panoskaltsis-Mortari A, Chung B, Danilenko D M, Farrell C, Lacey D L, Blazar B R, Weinberg K I. (2002) Protection from thymic epithelial cell injury by keratinocyte growth factor: a new approach to improve thymic and peripheral T-cell reconstitution after bone marrow transplantation. Blood. 15; 99(12):4592-600). However, in contrast to RANKL, Fgf-7 shows a protective but not a regenerative effect during BMT.

Nevertheless, we demonstrate that RANKL administration has beneficial effects on thymic recovery. Moreover, RANKL treatment in BM-transplanted LTα$^{-/-}$ mice had only minor effects on TEC regeneration, numbers of ETPs and strikingly de novo thymopoiesis was not ameliorated. Interestingly, whereas LTα is dispensable for Aire$^+$ mTEC differentiation at steady state (32), the regeneration of these cells induced by RANKL treatment critically depends on LTα. These data indicate that the mechanisms involved in Aire$^+$ mTEC regeneration are distinguishable from those implicated in their emergence/differentiation at steady state. Importantly, beneficial effects of RANKL treatment observed on TEC regeneration are likely not due to a direct action on TECs because the effects of RANKL on these cells were modest in absence of LTα. Thus, these data argue in favor of model in which RANKL acts indirectly on TECs through LTi cells that express LTα. This notion is supported by the fact that the turnover rate of mTECs is of around 2 weeks (54, 55) and thus it is unlikely that RANKL injected early after BMT still acts on mTECs two months later.

To avoid any potential side effects of the systemic administration of RANKL, such as osteoporosis, a possible strategy would be to deliver directly this molecule intrathymically in patients after cytoablative conditioning or combined RANKL with bisphosphonate to prevent bone resorption (57). The administration of bisphosphonate leads to a decrease in osteoclast differentiation and in apoptosis of mature osteoclasts. Importantly, this drug that inhibits bone resorption does not affect RANKL signaling (Kim Y H, Kim G S, Jeong-Hwa B (2002) Inhibitory action of bisphosphonates on bone resorption does not involve the regulation of RANKL and OPG expression. Exp Mol Med 34: 145-151; Verde M E, Bermejo D, Gruppi A, Grenon M (2015) Effect of Bisphosphonates on the Levels of Rankl and Opg in Gingival Crevicular Fluid of Patients With Periodontal Disease and Post-menopausal Osteoporosis. Acta Odontol Latinoam 28: 215-221). Furthermore, bisphosphonate combined with RANKL have been shown to suppress mouse and human osteoclast differentiation mediated by RANKL treatment (Tomimori Y, Mori K, Koide M, Nakamichi Y, Ninomiya T, Udagawa N, Yasuda H (2009) Evaluation of pharmaceuticals with a novel 50-hour animal model of bone loss. J Bone Miner Res 24: 1194-1205). Our data demonstrate that a co-treatment of risedronate and RANKL during BMT protects efficiently from bone resorption without interfering with RANKL beneficial effects on thymic regeneration. Thus, RANKL treatment in clinic is expected to be promising for enhancing the regeneration of immune functions in patients whose thymus has been severely damaged.

Interestingly, RANKL administration is also efficient for TEC and T-cell regeneration during BMT in older individuals in which thymic involution results in diminished TEC cellularity, disrupted thymic architecture and decreased T-cell output (45, 46). These results are of special interest for elderly patients in which the recovery of T-cell functions upon BMT is less efficient (44).

Age-induced thymic involution results in a reduced efficacy of the immune system to fight against opportunistic infections and also favors the development of autoimmunity and increases the incidence of cancer (Lynch H E, Goldberg G L, Chidgey A, Van den Brink M R, Boyd R, Sempowski G D (2009) Thymic involution and immune reconstitution. Trends Immunol. July; 30(7):366-73). Thymic function declines in the second year of life and is marked by a progressive diminution mainly in cTECs but also in mTECs (Steinmann G G, Klaus B, Müller-Hermelink H K (1985) The involution of the ageing human thymic epithelium is independent of puberty. A morphometric study. Scand J Immunol.; 22(5):563-75). The administration of insulin growth factor (IGF) or Ghrelin peptide hormone partly improves thymic compartments in aged mice (Montecino-Rodriguez E1, Clark R, Dorshkind K. (1998) Effects of insulin-like growth factor administration and bone marrow transplantation on thymopoiesis in aged mice. Endocrinology. 139(10):4120-6; Dixit V D, Yang H, Sun Y, Weeraratna A T, Youm Y H, Smith R G, Taub D D. (2007) Ghrelin promotes thymopoiesis during aging. J Clin Invest. 117(10): 2778-90). Fgf-7 plays also significant roles in the correction of thymus senescence in mice (Min D1, Panoskaltsis-Mortari A, Kuro-O M, Hollander G A, Blazar B R, Weinberg K I. (2007) Sustained thymopoiesis and improvement in functional immunity induced by exogenous KGF administration in murine models of aging. Blood. 5; 109(6):2529-37). However, the efficacy of Fgf-7 alone in clinical trials remains to be established. Our data demonstrate that a single three days course of RANKL in aged mice partially recovered the numbers of thymocytes until three weeks after treatment. Importantly, this treatment totally reversed the diminution of cTECs and mTECs but also ETPs observed upon thymic involution. Interestingly, we show that the expression of RANK is conserved in the thymic medulla in human, indicating that RANKL treatment could be also beneficial to restore thymic function in different clinical settings.

This study thus reveals that administration of RANKL offers an innovative therapeutic strategy to boost thymic recovery at several levels: TEC regeneration, thymus homing of T-cell progenitors and de novo thymopoïesis.

REFERENCES

Throughout this application, various references describe the state of the art to which this invention pertains. The disclosures of these references are hereby incorporated by reference into the present disclosure.

1. Anderson, G., and Takahama, Y. 2012. Thymic epithelial cells: working class heroes for T cell development and repertoire selection. *Trends in immunology* 33:256-263.
2. Derbinski, J., Schulte, A., Kyewski, B., and Klein, L. 2001. Promiscuous gene expression in medullary thymic epithelial cells mirrors the peripheral self. *Nat Immunol* 2:1032-1039.
3. Sansom, S. N., Shikama-Dorn, N., Zhanybekova, S., Nusspaumer, G., Macaulay, I. C., Deadman, M. E., Heger, A., Ponting, C. P., and Hollander, G. A. 2014. Population and single-cell genomics reveal the Aire dependency, relief from Polycomb silencing, and distribution of self-antigen expression in thymic epithelia. *Genome research.*
4. Anderson, M. S., Venanzi, E. S., Klein, L., Chen, Z., Berzins, S. P., Turley, S. J., von Boehmer, H., Bronson, R., Dierich, A., Benoist, C., et al. 2002. Projection of an immunological self shadow within the thymus by the aire protein. *Science* 298:1395-1401.
5. Takaba, H., Morishita, Y., Tomofuji, Y., Danks, L., Nitta, T., Komatsu, N., Kodama, T., and Takayanagi, H. 2015. Fezf2 Orchestrates a Thymic Program of Self-Antigen Expression for Immune Tolerance. *Cell* 163:975-987.
6. Lopes, N., Serge, A., Ferrier, P., and Irla, M. 2015. Thymic Crosstalk Coordinates Medulla Organization and T-Cell Tolerance Induction. *Frontiers in immunology* 6:365.
7. van Ewijk, W., Shores, E. W., and Singer, A. 1994. Crosstalk in the mouse thymus. *Immunol Today* 15:214-217.
8. van den Brink, M. R., Alpdogan, O., and Boyd, R. L. 2004. Strategies to enhance T-cell reconstitution in immunocompromised patients. *Nature reviews. Immunology* 4:856-867.
9. Fletcher, A. L., Lowen, T. E., Sakkal, S., Reiseger, J. J., Hammett, M. V., Seach, N., Scott, H. S., Boyd, R. L., and Chidgey, A. P. 2009. Ablation and regeneration of tolerance-inducing medullary thymic epithelial cells after cyclosporine, cyclophosphamide, and dexamethasone treatment. *Journal of immunology* 183:823-831.
10. Adkins, B., Gandour, D., Strober, S., and Weissman, I. 1988. Total lymphoid irradiation leads to transient depletion of the mouse thymic medulla and persistent abnormalities among medullary stromal cells. *Journal of immunology* 140:3373-3379.
11. Hollander, G. A., Krenger, W., and Blazar, B. R. 2010. Emerging strategies to boost thymic function. *Current opinion in pharmacology* 10:443-453.
12. Irla, M., Guenot, J., Sealy, G., Reith, W., Imhof, B. A., and Serge, A. 2013. Three-dimensional visualization of the mouse thymus organization in health and immunodeficiency. *Journal of immunology* 190:586-596.
13. Irifune, T., Tamechika, M., Adachi, Y., Tokuda, N., Sawada, T., and Fukumoto, T. 2004. Morphological and immunohistochemical changes to thymic epithelial cells in the irradiated and recovering rat thymus. *Archives of histology and cytology* 67:149-158.
14. Hakim, F. T., Cepeda, R., Kaimei, S., Mackall, C. L., McAtee, N., Zujewski, J., Cowan, K., and Gress, R. E. 1997. Constraints on CD4 recovery postchemotherapy in adults: thymic insufficiency and apoptotic decline of expanded peripheral CD4 cells. *Blood* 90:3789-3798.
15. Small, T. N., Papadopoulos, E. B., Boulad, F., Black, P., Castro-Malaspina, H., Childs, B. H., Collins, N., Gillio, A., George, D., Jakubowski, A., et al 1999. Comparison of immune reconstitution after unrelated and related T-cell-depleted bone marrow transplantation: effect of patient age and donor leukocyte infusions. *Blood* 93:467-480.
16. King, C., Ilic, A., Koelsch, K., and Sarvetnick, N. 2004. Homeostatic expansion of T cells during immune insufficiency generates autoimmunity. *Cell* 117:265-277.
17. Parkman, R., Cohen, G., Carter, S. L., Weinberg, K. I., Masinsin, B., Guinan, E., Kurtzberg, J., Wagner, J. E., and Kernan, N. A. 2006. Successful immune reconstitution decreases leukemic relapse and improves survival in recipients of unrelated cord blood transplantation. *Biology of blood and marrow transplantation: journal of the American Society for Blood and Marrow Transplantation* 12:919-927.
18. Curtis, R. E., Rowlings, P. A., Deeg, H. J., Shriner, D. A., Socie, G., Travis, L. B., Horowitz, M. M., Witherspoon, R. P., Hoover, R. N., Sobocinski, K. A., et al. 1997. Solid cancers after bone marrow transplantation. *The New England journal of medicine* 336:897-904.
19. Penit, C., and Ezine, S. 1989. Cell proliferation and thymocyte subset reconstitution in sublethally irradiated mice: compared kinetics of endogenous and intrathymically transferred progenitors. *Proceedings of the National Academy of Sciences of the United States of America* 86:5547-5551.
20. Zlotoff, D. A., Zhang, S. L., De Obaldia, M. E., Hess, P. R., Todd, S. P., Logan, T. D., and Bhandoola, A. 2011. Delivery of progenitors to the thymus limits T-lineage reconstitution after bone marrow transplantation. *Blood* 118:1962-1970.
21. Chen, B. J., Cui, X., Sempowski, G. D., Domen, J., and Chao, N. J. 2004. Hematopoietic stem cell dose correlates with the speed of immune reconstitution after stem cell transplantation. *Blood* 103:4344-4352.
22. Fata, J. E., Kong, Y. Y., Li, J., Sasaki, T., Irie-Sasaki, J., Moorehead, R. A., Elliott, R., Scully, S., Voura, E. B., Lacey, D. L., et al. 2000. The osteoclast differentiation factor osteoprotegerin-ligand is essential for mammary gland development. *Cell* 103:41-50.
23. Duheron, V., Hess, E., Duval, M., Decossas, M., Castaneda, B., Klopper, J. E., Amoasii, L., Barbaroux, J. B., Williams, I. R., Yagita, H., et al. 2011. Receptor activator of NF-kappaB (RANK) stimulates the proliferation of epithelial cells of the epidermo-pilosebaceous unit. *Proceedings of the National Academy of Sciences of the United States of America* 108:5342-5347.
24. Knoop, K. A., Kumar, N., Butler, B. R., Sakthivel, S. K., Taylor, R. T., Nochi, T., Akiba, H., Yagita, H., Kiyono, H., and Williams, I. R. 2009. RANKL is necessary and sufficient to initiate development of antigen-sampling M cells in the intestinal epithelium. *Journal of immunology* 183:5738-5747.
25. Rossi, S. W., Kim, M. Y., Leibbrandt, A., Parnell, S. M., Jenkinson, W. E., Glanville, S. H., McConnell, F. M., Scott, H. S., Penninger, J. M., Jenkinson, E. J., et al. 2007. RANK signals from CD4(+)3(−) inducer cells regulate development of Aire-expressing epithelial cells in the thymic medulla. *J Exp Med* 204:1267-1272.
26. Roberts, N. A., White, A. J., Jenkinson, W. E., Turchinovich, G., Nakamura, K., Withers, D. R., McConnell, F. M., Desanti, G. E., Benezech, C., Parnell, S. M., et al. 2012. Rank signaling links the development of invariant gammadelta T cell progenitors and Aire(+) medullary epithelium. *Immunity* 36:427-437.
27. Hikosaka, Y., Nitta, T., Ohigashi, I., Yano, K., Ishimaru, N., Hayashi, Y., Matsumoto, M., Matsuo, K., Penninger, J. M., Takayanagi, H., et al. 2008. The cytokine RANKL produced by positively selected thymocytes fosters medullary thymic epithelial cells that express autoimmune regulator. *Immunity* 29:438-450.
28. Akiyama, T., Shimo, Y., Yanai, H., Qin, J., Ohshima, D., Maruyama, Y., Asaumi, Y., Kitazawa, J., Takayanagi, H., Penninger, J. M., et al. 2008. The tumor necrosis factor family receptors RANK and CD40 cooperatively establish the thymic medullary microenvironment and self-tolerance. *Immunity* 29:423-437.
29. Irla, M., Hugues, S., Gill, J., Nitta, T., Hikosaka, Y., Williams, I. R., Hubert, F. X., Scott, H. S., Takahama, Y., Hollander, G. A., et al. 2008. Autoantigen-specific interactions with CD4+ thymocytes control mature medullary thymic epithelial cell cellularity. *Immunity* 29:451-463.

30. Irla, M., Hollander, G., and Reith, W. 2010. Control of central self-tolerance induction by autoreactive CD4+ thymocytes. *Trends in immunology* 31:71-79.
31. Ohigashi, I., Nitta, T., Lkhagvasuren, E., Yasuda, H., and Takahama, Y. 2011. Effects of RANKL on the thymic medulla. *European journal of immunology* 41:1822-1827.
32. Venanzi, E. S., Gray, D. H., Benoist, C., and Mathis, D. 2007. Lymphotoxin pathway and Aire influences on thymic medullary epithelial cells are unconnected. *J Immunol* 179:5693-5700.
33. Seach, N., Ueno, T., Fletcher, A. L., Lowen, T., Mattesich, M., Engwerda, C. R., Scott, H. S., Ware, C. F., Chidgey, A. P., Gray, D. H., et al. 2008. The lymphotoxin pathway regulates Aire-independent expression of ectopic genes and chemokines in thymic stromal cells. *J Immunol* 180:5384-5392.
34. De Togni, P., Goellner, J., Ruddle, N. H., Streeter, P. R., Fick, A., Mariathasan, S., Smith, S. C., Carlson, R., Shornick, L. P., Strauss-Schoenberger, J., et al. 1994. Abnormal development of peripheral lymphoid organs in mice deficient in lymphotoxin. *Science* 264:703-707.
35. Sun, Z., Unutmaz, D., Zou, Y. R., Sunshine, M. J., Pierani, A., Brenner-Morton, S., Mebius, R. E., and Littman, D. R. 2000. Requirement for RORgamma in thymocyte survival and lymphoid organ development. *Science* 288:2369-2373.
36. Wong, K., Lister, N. L., Barsanti, M., Lim, J. M., Hammett, M. V., Khong, D. M., Siatskas, C., Gray, D. H., Boyd, R. L., and Chidgey, A. P. 2014. Multilineage potential and self-renewal define an epithelial progenitor cell population in the adult thymus. *Cell reports* 8:1198-1209.
37. Yoshida, H., Naito, A., Inoue, J., Satoh, M., Santee-Cooper, S. M., Ware, C. F., Togawa, A., and Nishikawa, S. 2002. Different cytokines induce surface lymphotoxin-alphabeta on IL-7 receptor-alpha cells that differentially engender lymph nodes and Peyer's patches. *Immunity* 17:823-833.
38. Gommerman, J. L., and Browning, J. L. 2003. Lymphotoxin/light, lymphoid microenvironments and autoimmune disease. *Nature reviews. Immunology* 3:642-655.
39. Rossi, F. M., Corbel, S. Y., Merzaban, J. S., Carlow, D. A., Gossens, K., Duenas, J., So, L., Yi, L., and Ziltener, H. J. 2005. Recruitment of adult thymic progenitors is regulated by P-selectin and its ligand PSGL-1. *Nature immunology* 6:626-634.
40. Scimone, M. L., Aifantis, I., Apostolou, I., von Boehmer, H., and von Andrian, U. H. 2006. A multistep adhesion cascade for lymphoid progenitor cell homing to the thymus. *Proceedings of the National Academy of Sciences of the United States of America* 103:7006-7011.
41. Zlotoff, D. A., Sambandam, A., Logan, T. D., Bell, J. J., Schwarz, B. A., and Bhandoola, A. 2010. CCR7 and CCR9 together recruit hematopoietic progenitors to the adult thymus. *Blood* 115:1897-1905.
42. Krueger, A., Willenzon, S., Lyszkiewicz, M., Kremmer, E., and Forster, R. 2010. CC chemokine receptor 7 and 9 double-deficient hematopoietic progenitors are severely impaired in seeding the adult thymus. *Blood* 115:1906-1912.
43. Dudakov, J. A., Hanash, A. M., Jenq, R. R., Young, L. F., Ghosh, A., Singer, N. V., West, M. L., Smith, O. M., Holland, A. M., Tsai, J. J., et al. 2012. Interleukin-22 drives endogenous thymic regeneration in mice. *Science* 336:91-95.
44. Toubert, A., Glauzy, S., Douay, C., and Clave, E. 2012. Thymus and immune reconstitution after allogeneic hematopoietic stem cell transplantation in humans: never say never again. *Tissue antigens* 79:83-89.
45. Gray, D. H., Seach, N., Ueno, T., Milton, M. K., Liston, A., Lew, A. M., Goodnow, C. C., and Boyd, R. L. 2006. Developmental kinetics, turnover, and stimulatory capacity of thymic epithelial cells. *Blood* 108:3777-3785.
46. Ki, S., Park, D., Selden, H. J., Seita, J., Chung, H., Kim, J., Iyer, V. R., and Ehrlich, L. I. 2014. Global transcriptional profiling reveals distinct functions of thymic stromal subsets and age-related changes during thymic involution. *Cell reports* 9:402-415.
47. Yoshida, H., Honda, K., Shinkura, R., Adachi, S., Nishikawa, S., Maki, K., Ikuta, K., and Nishikawa, S. I. 1999. IL-7 receptor alpha+ CD3(-) cells in the embryonic intestine induces the organizing center of Peyer's patches. *International immunology* 11:643-655.
48. Lind, E. F., Prockop, S. E., Porritt, H. E., and Petrie, H. T. 2001. Mapping precursor movement through the postnatal thymus reveals specific microenvironments supporting defined stages of early lymphoid development. *The Journal of experimental medicine* 194:127-134.
49. Lucas, B., James, K. D., Cosway, E. J., Parnell, S. M., Tumanov, A. V., Ware, C. F., Jenkinson, W. E., and Anderson, G. 2016. Lymphotoxin beta Receptor Controls T Cell Progenitor Entry to the Thymus. *Journal of immunology*.
50. Shi, Y., Wu, W., Chai, Q., Li, Q., Hou, Y., Xia, H., Ren, B., Xu, H., Guo, X., Jin, C., et al. 2016. LTbetaR controls thymic portal endothelial cells for haematopoietic progenitor cell homing and T-cell regeneration. *Nature communications* 7:12369.
51. Boehm, T., Scheu, S., Pfeffer, K., and Bleul, C. C. 2003. Thymic medullary epithelial cell differentiation, thymocyte emigration, and the control of autoimmunity require lympho-epithelial cross talk via LTbetaR. *J Exp Med* 198:757-769.
52. Irla, M., Guerri, L., Guenot, J., Serge, A., Lantz, O., Liston, A., Imhof, B. A., Palmer, E., and Reith, W. 2012. Antigen recognition by autoreactive cd4(+) thymocytes drives homeostasis of the thymic medulla. *PLoS One* 7:e52591.
53. Kong, Y. Y., Yoshida, H., Sarosi, I., Tan, H. L., Timms, E., Capparelli, C., Morony, S., Oliveira-dos-Santos, A. J., Van, G., Itie, A., et al. 1999. OPGL is a key regulator of osteoclastogenesis, lymphocyte development and lymph-node organogenesis. *Nature* 397:315-323.
54. Gabler, J., Arnold, J., and Kyewski, B. 2007. Promiscuous gene expression and the developmental dynamics of medullary thymic epithelial cells. *Eur J Immunol* 37:3363-3372.
55. Gray, D., Abramson, J., Benoist, C., and Mathis, D. 2007. Proliferative arrest and rapid turnover of thymic epithelial cells expressing Aire. *J Exp Med* 204:2521-2528.
56. Chinn, I. K., Blackburn, C. C., Manley, N. R., and Sempowski, G. D. 2012. Changes in primary lymphoid organs with aging. *Seminars in immunology* 24:309-320.
57. Tomimori, Y., Mori, K., Koide, M., Nakamichi, Y., Ninomiya, T., Udagawa, N., and Yasuda, H. 2009. Evaluation of pharmaceuticals with a novel 50-hour animal model of bone loss. *Journal of bone and mineral research: the official journal of the American Society for Bone and Mineral Research* 24:1194-1205.
58. van de Pavert, S. A., Ferreira, M., Domingues, R. G., Ribeiro, H., Molenaar, R., Moreira-Santos, L., Almeida, F. F., Ibiza, S., Barbosa, I., Goverse, G., et al. 2014. Maternal retinoids control type 3 innate lymphoid cells and set the offspring immunity. *Nature* 508:123-127.
59. Serge, A., Bailly, A. L., Aurrand-Lions, M., Imhof, B. A., and Irla, M. 2015. For3D: Full Organ Reconstruction in 3D, an Automated Tool for Deciphering the Complexity of Lymphoid Organs. *Journal of immunological methods*.

The invention claimed is:

1. A method of boosting thymic regeneration in a patient suffering from a thymic injury comprising:
   performing a bone marrow or stem cell transplantation, wherein the patient is a recipient of the bone marrow or stem cells;
   administering intrathymically to the patient a therapeutically effective amount of a RANKL polypeptide sufficient to boost thymic generation, wherein the RANKL polypeptide is the only active agent stimulating thymic cells; and
   administering an amount of a bisphosphonate sufficient to inhibit bone resorption.

2. The method of claim 1 wherein the thymic injury is selected from the group consisting of cytoablative therapy, complications related to HIV/AIDS, aging process, malnutrition, and radiation poisoning due to nuclear disaster.

3. The method of claim 1 wherein the patient is selected from the group consisting of children, young adults, middle aged adults, and elderly adults.

4. The method of claim 1 wherein the patient suffers from a cancer and has undergone a cytoablative therapy which caused the thymic injury.

5. The method of claim 4 wherein the cytoablative therapy is radiotherapy or chemotherapy.

6. The method of claim 1 wherein the RANKL polypeptide is a polypeptide comprising an amino acid sequence having at least 80% of identity with SEQ ID NO:1 or SEQ ID NO:2.

7. The method of claim 1 wherein the RANKL polypeptide is fused to an immunoglobulin domain to form an immunoadhesin.

8. The method of claim 1, wherein the thymic injury is due to cytoablative conditioning and the step of administering RANKL prevents immunodeficiency caused by the cytoablative conditioning.

9. The method of claim 1 wherein the thymic injury is thymic involution due to aging.

10. A method for boosting thymic regeneration comprising a treatment to delay the onset, reduce the severity of or ameliorate one or more symptoms of an infectious disease, autoimmunity or cancer relapse in a subject in need thereof comprising administering intrathymically to the subject a therapeutically effective amount of a RANKL polypeptide, wherein the RANKL polypeptide is the only active agent stimulating thymic cells and wherein the RANKL polypeptide is administered to the subject in combination with an amount of a bisphosphonate sufficient to inhibit bone resorption.

11. The method according to claim 1 wherein the patient is a human.

12. The method of claim 7, wherein the immunoglobulin domain is a Fc region.

13. The method of claim 10, wherein the step of administering boosts or enhances long-term recovery of T-cell functions.

14. The method of claim 1, wherein the RANKL polypeptide has the amino acid identity of SEQ ID NO:1 or SEQ ID NO: 2.

15. The method of claim 10, wherein the RANKL polypeptide has the amino acid identity of SEQ ID NO:1 or SEQ ID NO: 2.

16. The method of claim 10, wherein the RANKL polypeptide is administered to the subject in combination with an amount of a bisphosphonate sufficient to inhibit bone resorption.

17. A method of boosting thymic regeneration in a bone marrow or stem cell transplantation recipient subject, comprising the steps of
performing a cytoablative treatment, wherein the cytoablative treatment severely affects thymic cells in the subject,
delivering the bone marrow or stem cell transplantation to the subject, and
administering intrathymically to the subject therapeutically effective amounts of a RANKL polypeptide having the amino acid sequence identity of SEQ ID NO:1 or SEQ ID NO:2, wherein the RANKL polypeptide as a sole active agent stimulating thymic cells to boost thymic regeneration.

18. The method of claim 17, wherein the RANKL polypeptide is administered to the subject in combination with an amount of a bisphosphonate sufficient to inhibit bone resorption.

19. The method of claim 1, wherein the therapeutically effective amount of the RANKL polypeptide is at least 5 mg/kg of body weight.

20. The method of claim 10, wherein the therapeutically effective amount of the RANKL polypeptide is at least 5 mg/kg of body weight.

21. The method of claim 17, wherein the therapeutically effective amount of the RANKL polypeptide is at least 5 mg/kg of body weight.

\* \* \* \* \*

SEQUENCE LISTING

<160> NUMBER OF SEQ ID NOS: 2

<210> SEQ ID NO 1
<211> LENGTH: 317
<212> TYPE: PRT
<213> ORGANISM: Homo sapiens

<400> SEQUENCE: 1

```
Met Arg Arg Ala Ser Arg Asp Tyr Thr Lys Tyr Leu Arg Gly Ser Glu
1               5                  10                  15

Glu Met Gly Gly Gly Pro Gly Ala Pro His Glu Gly Pro Leu His Ala
            20                  25                  30

Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
        275                 280                 285

Ile Ser Ile Glu Val Ser Asn Pro Ser Leu Leu Asp Pro Asp Gln Asp
290                 295                 300

Ala Thr Tyr Phe Gly Ala Phe Lys Val Arg Asp Ile Asp
305                 310                 315
```

<210> SEQ ID NO 2
<211> LENGTH: 244
<212> TYPE: PRT
<213> ORGANISM: Homo sapiens

<400> SEQUENCE: 2

Met Asp Pro Asn Arg Ile Ser Glu Asp Gly Thr His Cys Ile Tyr Arg

```
1               5                   10                  15
Ile Leu Arg Leu His Glu Asn Ala Asp Phe Gln Asp Thr Thr Leu Glu
            20                  25                  30

Ser Gln Asp Thr Lys Leu Ile Pro Asp Ser Cys Arg Arg Ile Lys Gln
            35                  40                  45

Ala Phe Gln Gly Ala Val Gln Lys Glu Leu Gln His Ile Val Gly Ser
        50                  55                  60

Gln His Ile Arg Ala Glu Lys Ala Met Val Asp Gly Ser Trp Leu Asp
65                  70                  75                  80

Leu Ala Lys Arg Ser Lys Leu Glu Ala Gln Pro Phe Ala His Leu Thr
            85                  90                  95

Ile Asn Ala Thr Asp Ile Pro Ser Gly Ser His Lys Val Ser Leu Ser
            100                 105                 110

Ser Trp Tyr His Asp Arg Gly Trp Ala Lys Ile Ser Asn Met Thr Phe
            115                 120                 125

Ser Asn Gly Lys Leu Ile Val Asn Gln Asp Gly Phe Tyr Tyr Leu Tyr
            130                 135                 140

Ala Asn Ile Cys Phe Arg His His Glu Thr Ser Gly Asp Leu Ala Thr
145                 150                 155                 160

Glu Tyr Leu Gln Leu Met Val Tyr Val Thr Lys Thr Ser Ile Lys Ile
            165                 170                 175

Pro Ser Ser His Thr Leu Met Lys Gly Gly Ser Thr Lys Tyr Trp Ser
            180                 185                 190

Gly Asn Ser Glu Phe His Phe Tyr Ser Ile Asn Val Gly Gly Phe Phe
            195                 200                 205

Lys Leu Arg Ser Gly Glu Glu Ile Ser Ile Glu Val Ser Asn Pro Ser
            210                 215                 220

Leu Leu Asp Pro Asp Gln Asp Ala Thr Tyr Phe Gly Ala Phe Lys Val
225                 230                 235                 240

Arg Asp Ile Asp
```